(12) United States Patent
Pirrung

(10) Patent No.: US 9,399,627 B2
(45) Date of Patent: Jul. 26, 2016

(54) SUBSTITUTED MACROCYCLIC COMPOUNDS HAVING PROTEASOME INHIBITORY ACTIVITY

(71) Applicant: THE REGENTS OF THE UNIVERSITY OF CALIFORNIA, Oakland, CA (US)

(72) Inventor: Michael C. Pirrung, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/408,140

(22) PCT Filed: Jun. 14, 2013

(86) PCT No.: PCT/US2013/045854
§ 371 (c)(1),
(2) Date: Dec. 15, 2014

(87) PCT Pub. No.: WO2013/188750
PCT Pub. Date: Dec. 19, 2013

(65) Prior Publication Data
US 2015/0141392 A1 May 21, 2015

Related U.S. Application Data

(60) Provisional application No. 61/660,585, filed on Jun. 15, 2012.

(51) Int. Cl.
*C07D 245/02* (2006.01)
*A61K 31/395* (2006.01)
*C07D 403/12* (2006.01)
*A61K 45/06* (2006.01)

(52) U.S. Cl.
CPC .......... *C07D 245/02* (2013.01); *A61K 31/395* (2013.01); *A61K 45/06* (2013.01); *C07D 403/12* (2013.01)

(58) Field of Classification Search
CPC .................................................. C07D 245/02
See application file for complete search history.

(56) References Cited

FOREIGN PATENT DOCUMENTS

| WO | 2009/065090 A2 | 5/2009 |
| WO | WO 2010/081731 * | 1/2010 |
| WO | 2011/069045 A2 | 6/2011 |

OTHER PUBLICATIONS

Anshu et al., "Novel proteasome-inhibitory syrbactin analogs inducing endoplasmic reticulum stress and apoptosis in hematological tumor cell lines," Biochemical Pharmacology, Jun. 28, 2011, pp. 600-609, vol. 82, No. 6.
Archer et al., "Syrbactin class proteasome inhibitor-induced apoptosis and autophagy occurs in association with p53 accumulation and Akt/PKB activation in neuroblastoma," Biochemical Pharmacology, 2010, pp. 170-178, vol. 80, No. 2.
Clerc et al., "Synthetic and structural studies on syringolin A and B reveal critical determinants of selectivity and potency of proteasome inhibition," Proc. Natl. Acad. Sci. USA, Apr. 21, 2009, pp. 6507-6512, vol. 106, No. 16.
International Search Report and Written Opinion, Korean Intellectual Property Office, PCT/US2013/045854, Nov. 28, 2013.
International Preliminary Report on Patentability, PCT/US2013/045854, The International Bureau of WIPO, Date of Mailing: Dec. 24, 2014.
Archer, Crystal R. et al., "Activity Enhancement of the Synthetic Syrbactin Proteasome Inhibitor Hybrid and Biological Evaluation in Tumor Cells", Biochemistry, 2012, 51, 6880-6888.

* cited by examiner

*Primary Examiner* — Bruck Kifle
(74) *Attorney, Agent, or Firm* — Joseph R. Baker, Jr.; Gavrilovich, Dodd & Lindsey LLP

(57) ABSTRACT

The disclosure provides for novel compounds which have proteasome inhibitory activity, pharmaceutical compositions made thereof, and methods of use thereof to treat various disorders, including cancer and nonmalignant tumors.

15 Claims, 14 Drawing Sheets

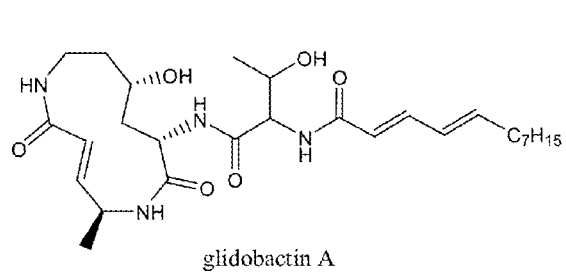
glidobactin A
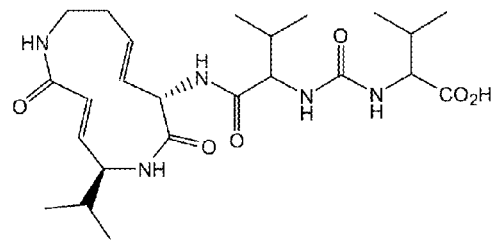
syringolin A
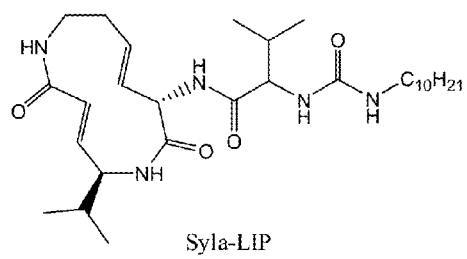
Syla-LIP
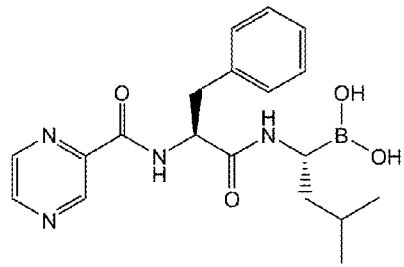
bortezomib
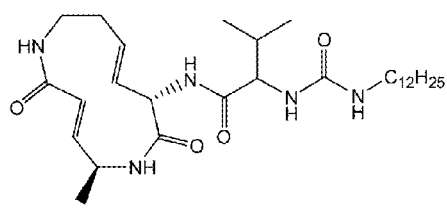
TIR-199
FIGURE 1

|  | Time | Ctrl | Mean Optical Densities | | | | | Log10 Concentration Percent Growth | | | | | GI50 | TGI | LC50 |
|---|---|---|---|---|---|---|---|---|---|---|---|---|---|---|---|
| Panel/Cell Line | Zero |  | -8.0 | -7.0 | -6.0 | -5.0 | -4.0 | -8.0 | -7.0 | -6.0 | -5.0 | -4.0 |  |  |  |
| Non-Small Cell Lung Cancer | | | | | | | | | | | | | | | |
| A549/ATCC | 0.296 | 1.481 | 1.479 | 1.064 | 0.427 | 0.297 | 0.369 | 100 | 65 | 11 |  | 6 | 1.89E-7 | > 1.00E-4 | > 1.00E-4 |
| EKVX | 0.426 | 1.256 | 1.220 | 0.922 | 0.583 | 0.374 | 0.480 | 96 | 60 | 20 | -12 | 7 | 1.76E-7 |  | > 1.00E-4 |
| HOP-62 | 0.454 | 1.006 | 0.987 | 0.271 | 0.064 | 0.063 | 0.056 | 96 | -40 | -86 | -86 | -88 | 2.19E-8 | 5.07E-8 | 1.82E-7 |
| NCI-H226 | 0.526 | 1.061 | 0.934 | 0.955 | 0.375 | 0.205 | 0.258 | 78 | 50 | -29 | -61 | -51 | 1.89E-7 | 5.45E-7 | 4.56E-6 |
| NCI-H23 | 0.648 | 2.222 | 1.921 | 1.066 | 0.877 | 0.456 | 0.452 | 81 | 27 | 15 | -30 | -30 | 3.70E-8 | 2.13E-6 | > 1.00E-4 |
| NCI-H322M | 0.746 | 1.816 | 1.874 | 1.662 | 1.193 | 1.052 | 0.892 | 105 | 95 | 42 | 29 | 14 | 6.43E-7 | > 1.00E-4 | > 1.00E-4 |
| NCI-H522 | 0.682 | 1.435 | 1.387 | 0.805 | 0.401 | 0.238 | 0.180 | 91 | -11 | -41 | -65 | -74 | 2.51E-8 | 7.75E-8 | 2.32E-6 |
| Colon Cancer | | | | | | | | | | | | | | | |
| COLO 205 | 0.316 | 1.150 | 1.022 | 0.271 | 0.197 | 0.184 | 0.091 | 85 | -14 | -38 | -42 | -71 | 2.24E-8 | 7.18E-8 | 1.90E-5 |
| HCC-2998 | 0.382 | 1.263 | 1.320 | 0.150 | 0.057 | 0.050 | 0.027 | 104 | -61 | -85 | -87 | -93 | 2.13E-8 | 4.27E-8 | 8.59E-8 |
| HCT-116 | 0.236 | 1.744 | 1.431 | 0.358 | 0.109 | 0.037 | 0.042 | 79 | 8 | -54 | -84 | -82 | 2.58E-8 | 1.35E-7 | 8.61E-7 |
| HCT-15 | 0.426 | 2.469 | 2.462 | 2.464 | 1.571 | 0.795 | 0.592 | 101 | 100 | 58 | 18 | 8 | 1.44E-6 | > 1.00E-4 | > 1.00E-4 |
| HT29 | 0.249 | 1.313 | 0.599 | 0.287 | 0.246 | 0.234 | 0.204 | 33 | 4 | -1 | -6 | -18 | < 1.00E-8 | 5.60E-7 | > 1.00E-4 |
| KM12 | 0.625 | 2.626 | 2.201 | 0.328 | 0.285 | 0.372 | 0.417 | 79 | -48 | -54 | -41 | -33 | 1.69E-8 | 4.20E-8 |  |
| CNS Cancer | | | | | | | | | | | | | | | |
| SF-268 | 0.528 | 1.720 | 1.706 | 0.672 | 0.454 | 0.578 | 0.695 | 99 | 12 | -14 | 4 | 14 | 3.66E-8 |  | > 1.00E-4 |
| SF-295 | 0.834 | 2.430 | 2.358 | 1.818 | 0.711 | 0.467 | 0.208 | 95 | 82 | -15 | -44 | -75 | 1.42E-7 | 6.40E-7 | 1.55E-5 |
| SNB-19 | 0.551 | 1.874 | 1.616 | 1.094 | 0.913 | 0.671 | 0.752 | 80 | 41 | 27 | 9 | 15 | 5.92E-8 | > 1.00E-4 | > 1.00E-4 |
| SNB-75 | 0.716 | 1.271 | 1.185 | 0.462 | 0.089 | 0.012 | 0.011 | 84 | -35 | -88 | -98 | -98 | 1.94E-8 | 5.06E-8 | 1.90E-7 |
| U251 | 0.365 | 1.783 | 1.714 | 0.441 | 0.247 | 0.097 | 0.130 | 95 | 5 | -32 | -73 | -64 | 3.18E-8 | 1.38E-7 | 2.69E-6 |
| Melanoma | | | | | | | | | | | | | | | |
| LOX IMVI | 0.286 | 2.378 | 2.263 | 1.287 | 0.153 | 0.140 | 0.082 | 96 | 48 | -47 | -51 | -72 | 9.00E-8 | 3.21E-7 | 5.38E-6 |
| MALME-3M | 0.749 | 1.569 | 1.568 | 1.304 | 1.069 | 0.839 | 0.738 | 103 | 88 | 39 | -15 | -2 | 4.11E-7 | 5.31E-6 | > 1.00E-4 |
| M14 | 0.429 | 1.605 | 1.608 | 1.220 | 0.650 | 0.516 | 0.275 | 100 | 67 | 19 | 7 | -36 | 2.27E-7 | 1.48E-5 | > 1.00E-4 |
| MDA-MB-435 | 0.561 | 2.283 | 1.957 | 0.591 | 0.454 | 0.204 | 0.142 | 81 | 2 | -19 | -64 | -75 | 2.46E-8 | 1.21E-7 | 4.92E-6 |
| SK-MEL-2 | 0.914 | 1.560 | 1.615 | 1.302 | 0.713 | 0.512 | 0.354 | 108 | 60 | -22 | -44 | -61 | 1.33E-7 | 5.39E-7 | 2.21E-5 |
| SK-MEL-28 | 0.333 | 0.957 | 0.964 | 0.676 | 0.085 | 0.022 | 0.021 | 101 | 55 | -75 | -93 | -94 | 1.08E-7 | 2.65E-7 | 6.46E-7 |
| SK-MEL-5 | 0.584 | 2.255 | 2.143 | 1.866 | 0.180 | 0.024 | 0.004 | 93 | 64 | -73 | -96 | -99 | 1.27E-7 | 2.94E-7 | 6.83E-7 |
| UACC-257 | 0.593 | 1.304 | 1.272 | 1.087 | 0.753 | 0.466 | 0.398 | 95 | 70 | 22 | -21 | -33 | 2.60E-7 | 3.25E-6 | > 1.00E-4 |
| UACC-62 | 0.632 | 2.193 | 2.019 | 0.582 | 0.228 | 0.104 | 0.056 | 89 | -8 | -64 | -84 | -91 | 2.52E-8 | 8.27E-8 | 5.64E-7 |
| Ovarian Cancer | | | | | | | | | | | | | | | |
| IGROV1 | 0.402 | 1.355 | 0.913 | 0.442 | 0.351 | 0.195 | 0.307 | 54 | 4 | -13 | -52 | -24 | 1.18E-8 | 1.76E-7 |  |
| OVCAR-3 | 0.491 | 1.474 | 1.514 | 0.620 | 0.665 | 0.539 | 0.258 | 104 | 13 | 18 | 5 | -47 | 3.93E-8 | 1.24E-5 | > 1.00E-4 |
| OVCAR-4 | 0.565 | 1.182 | 1.188 | 0.700 | 0.583 | 0.325 | 0.590 | 101 | 22 | 3 | -43 | 4 | 4.41E-8 |  | > 1.00E-4 |
| OVCAR-5 | 0.696 | 1.509 | 1.485 | 0.746 | 0.427 | 0.285 | 0.173 | 97 | 16 | -28 | -52 | -71 | 3.85E-8 | 2.33E-7 | 8.10E-6 |
| NCI/ADR-RES | 0.456 | 1.792 | 1.740 | 1.692 | 1.540 | 1.428 | 1.183 | 96 | 93 | 81 | 73 | 54 | > 1.00E-4 | > 1.00E-4 | > 1.00E-4 |
| SK-OV-3 | 0.592 | 1.253 | 1.312 | 1.134 | 0.580 | 0.159 | 0.329 | 109 | 82 | -2 | -73 | -44 | 2.40E-7 | 9.44E-7 |  |
| Renal Cancer | | | | | | | | | | | | | | | |
| 786-0 | 0.581 | 2.062 | 2.109 | 1.328 | 0.643 | 0.296 | 0.267 | 103 | 50 | 4 | -49 | -54 | 1.02E-7 | 1.20E-6 | 1.54E-5 |
| ACHN | 0.398 | 1.643 | 1.724 | 1.868 | 0.968 | 0.642 | 0.594 | 106 | 102 | 46 | 20 | 16 | 8.40E-7 | > 1.00E-4 | > 1.00E-4 |
| CAKI-1 | 0.744 | 1.936 | 1.884 | 1.871 | 1.628 | 1.020 | 0.901 | 96 | 95 | 74 | 23 | 13 | 2.97E-6 | > 1.00E-4 | > 1.00E-4 |
| RXF 393 | 0.627 | 1.069 | 0.802 | 0.214 | 0.111 | 0.102 | 0.044 | 40 | -56 | -82 | -84 | -93 | < 1.00E-8 | 2.37E-8 | 7.07E-8 |
| SN12C | 0.596 | 2.314 | 2.230 | 1.828 | 0.401 | 0.104 | 0.076 | 95 | 72 | -33 | -83 | -87 | 1.81E-7 | 4.86E-7 | 2.22E-6 |
| TK-10 | 0.591 | 1.204 | 1.152 | 0.764 | 0.521 | 0.441 | 0.365 | 92 | 27 | -12 | -25 | -35 | 4.35E-8 | 4.91E-7 | > 1.00E-4 |
| UO-31 | 0.572 | 1.707 | 1.583 | 1.634 | 1.586 | 1.459 | 1.021 | 89 | 94 | 89 | 78 | 40 | 5.36E-5 | > 1.00E-4 | > 1.00E-4 |
| Prostate Cancer | | | | | | | | | | | | | | | |
| PC-3 | 0.381 | 1.766 | 0.996 | 0.373 | 0.295 | 0.213 | 0.260 | 44 | -2 | -23 | -44 | -32 | < 1.00E-8 | 9.01E-8 | > 1.00E-4 |
| DU-145 | 0.556 | 1.809 | 1.731 | 1.057 | 0.837 | 0.755 | 0.497 | 94 | 40 | 22 | 16 | -11 | 6.51E-8 | 3.98E-5 | > 1.00E-4 |
| Breast Cancer | | | | | | | | | | | | | | | |
| MCF7 | 0.299 | 1.631 | 1.491 | 0.732 | 0.495 | 0.267 | 0.223 | 89 | 33 | 15 | -11 | -26 | 4.93E-8 | 3.76E-6 | > 1.00E-4 |
| MDA-MB-231/ATCC | 0.504 | 1.135 | 1.148 | 0.680 | 0.288 | 0.217 | 0.170 | 102 | 28 | -43 | -57 | -66 | 5.04E-8 | 2.48E-7 | 3.19E-6 |
| BT-549 | 0.873 | 1.699 | 1.529 | 0.837 | 0.533 | 0.549 | 0.334 | 79 | -4 | -39 | -37 | -62 | 2.25E-8 | 8.93E-8 | 3.33E-5 |
| T-47D | 0.585 | 1.604 | 1.630 | 1.162 | 0.235 | 0.234 | 0.272 | 102 | 57 | -60 | -60 | -54 | 1.14E-7 | 3.08E-7 | 8.23E-7 |
| MDA-MB-468 | 0.583 | 1.152 | 1.011 | 0.596 | 0.217 | 0.148 | 0.137 | 75 | 2 | -63 | -75 | -77 | 2.22E-8 | 1.08E-7 | 6.36E-7 |

SUBSTITUTED MACROCYCLIC COMPOUNDS HAVING PROTEASOME INHIBITORY ACTIVITY

CROSS REFERENCE TO RELATED APPLICATIONS

This application is a U.S. National Stage Application filed under 35 U.S.C. §371 and claims priority to International Application No. PCT/US2013/045854, filed Jun. 14, 2013, which application claims priority under 35 U.S.C. §119 from Provisional Application Ser. No. 61/660,585 filed Jun. 15, 2012, the disclosures of which are incorporated herein by reference.

TECHNICAL FIELD

The disclosure provides synthesis schemes and methods to generate compounds having proteasome inhibitory activity, and the use of these compounds in treating various disorders, such as cancer and nonmalignant tumors.

BACKGROUND

The syringolin and glidobactin natural products are irreversible inhibitors of the proteasome. Proteasome inhibitors have been shown to exert beneficial biological effects when administered to subjects.

SUMMARY

The disclosure provides for compounds having proteasome inhibitory activity. These compounds were found to have unexpected therapeutic properties. The compounds disclosed herein are useful for treating any disorder that is associated with proteasome activity. In particular, the compounds of the disclosure can be used to treat disorders, such as cancer, nonmalignant tumors, autoimmune disorders, inflammatory disorders, disorders which respond favorably to immune suppression, and disorders resulting from Eubacteria, Archaebacteria, Fungi, Protists, and arthropod infections.

The disclosure further provides novel methods and reaction schemes to generate compounds or compound intermediates, such as the macrocyclic core structure of glidobactin. Compounds of the disclosure can be prepared using the methods and reactions disclosed herein in just a few steps, in high efficiency, and in good quantity. Therefore, the methods of the disclosure can be utilized in economically viable manufacturing processes.

In a particular embodiment, the disclosure provides for a compound comprising a structure of Formula II(a):

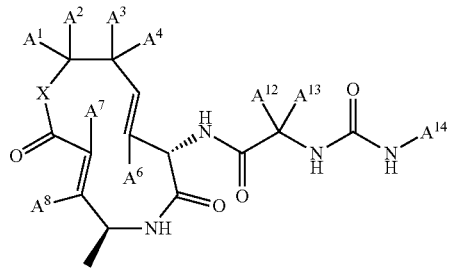

Formula II (a)

or a pharmaceutically acceptable salt, solvate or prodrug thereof, wherein:

X is N, O or S;

$A^1$-$A^4$ are each independently selected from the group comprising hydrogen, deuterium, FG, optionally substituted ($C_1$-$C_6$)alkyl, optionally substituted ($C_1$-$C_6$)alkenyl, optionally substituted ($C_1$-$C_6$)alkynyl, optionally substituted ($C_1$-$C_6$)hetero-alkyl, optionally substituted ($C_1$-$C_6$)hetero-alkenyl, optionally substituted ($C_1$-$C_5$)hetero-alkynyl, and $A^1$ and $A^4$ can be linked together to form an optionally substituted ring selected from cycloalkyl, heterocycle, and aryl.

$A^6$-$A^8$ are each independently selected from the group comprising hydrogen, deuterium, hydroxyl, halo, cyano, amino, nitro, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$)hetero-alkenyl, and optionally substituted ($C_1$-$C_3$)hetero-alkynyl;

$A^{12}$ is selected from the group comprising hydrogen, deuterium, hydroxyl, halo, cyano, amino, amide, carboxylic acid, nitro, ether, ester, optionally substituted ($C_1$-$C_8$)alkyl, optionally substituted ($C_1$-$C_8$)alkenyl, optionally substituted ($C_1$-$C_8$)alkynyl, optionally substituted ($C_1$-$C_7$)hetero-alkyl, optionally substituted ($C_1$-$C_7$)hetero-alkenyl, optionally substituted ($C_1$-$C_7$)hetero-alkynyl, optionally substituted cycloalkyl, optionally substituted aryl, and optionally substituted heterocycle;

$A^{13}$ is selected from the group comprising hydrogen, deuterium, hydroxyl, halo, cyano, amino, amide, carboxylic acid, nitro, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$)hetero-alkenyl, optionally substituted ($C_1$-$C_3$)hetero-alkynyl, optionally substituted cycloalkyl, optionally substituted aryl, and optionally substituted heterocycle, and $A^{12}$ and $A^{13}$ can be linked together to form an optionally substituted ring selected from cycloalkyl, heterocycle, and aryl; and $A^{14}$ is selected from the group comprising hydrogen, deuterium, FG, optionally substituted ($C_1$-$C_{16}$)alkyl, optionally substituted ($C_1$-$C_{16}$)alkenyl, optionally substituted ($C_1$-$C_{16}$)alkynyl, optionally substituted ($C_1$-$C_{15}$)hetero-alkyl, optionally substituted ($C_1$-$C_{15}$)hetero-alkenyl, optionally substituted ($C_1$-$C_{15}$)hetero-alkynyl, optionally substituted cycloalkyl, optionally substituted aryl, and optionally substituted heterocycle. In a further embodiment, the disclosure provides for a compound having the structure of:

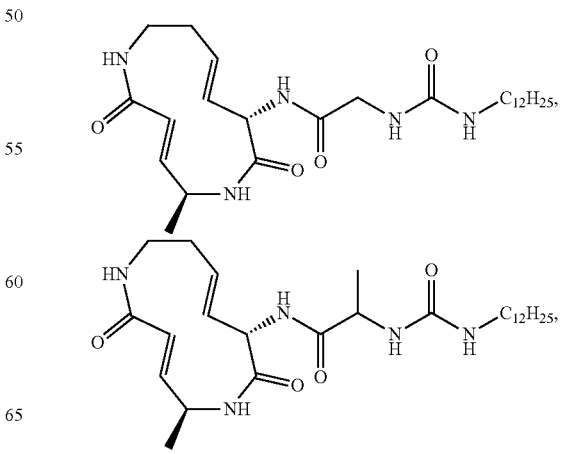

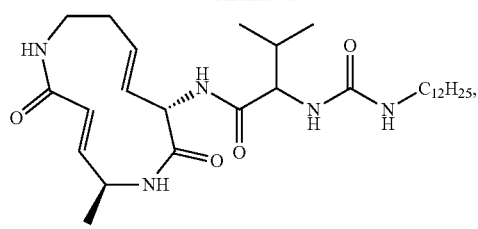
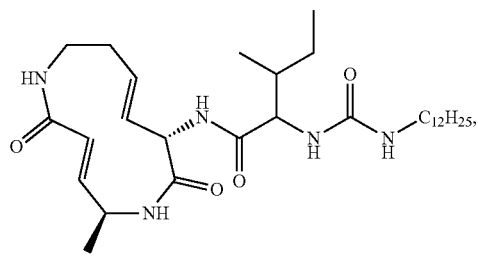
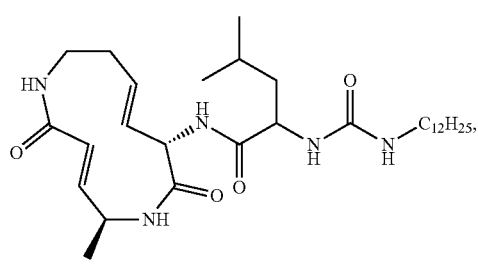
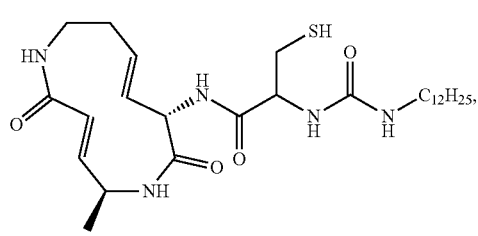
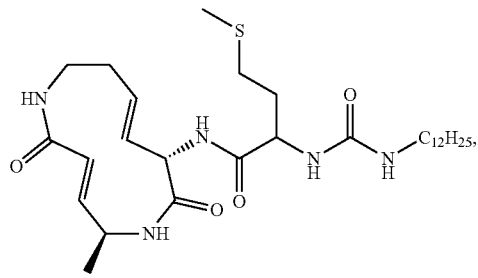
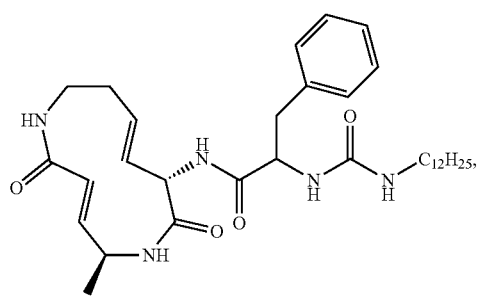
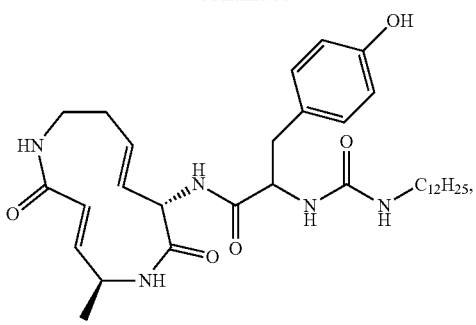
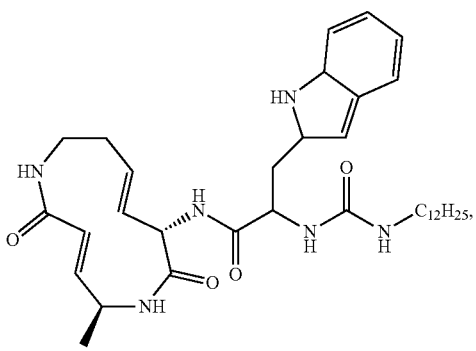
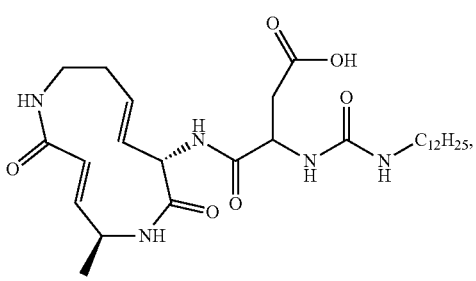
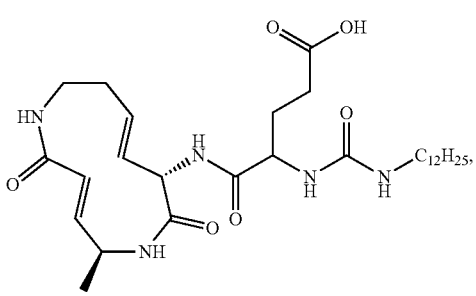
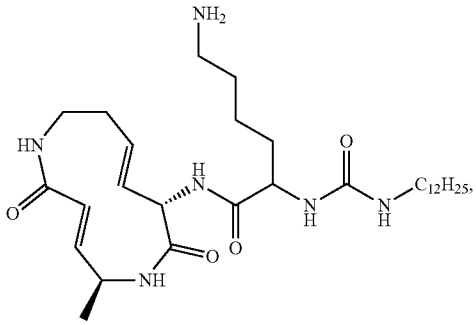

-continued

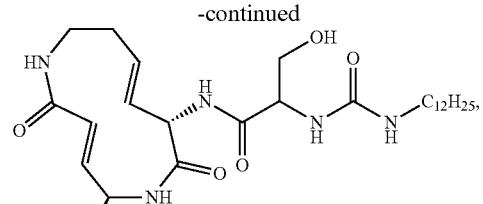

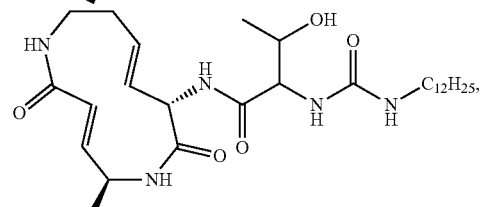

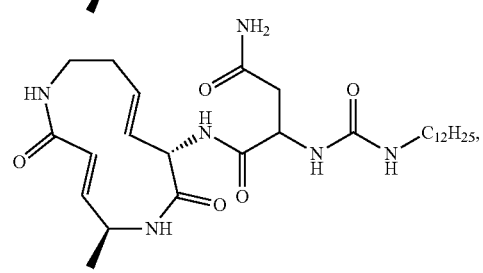

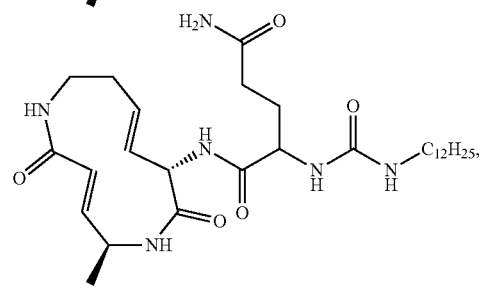

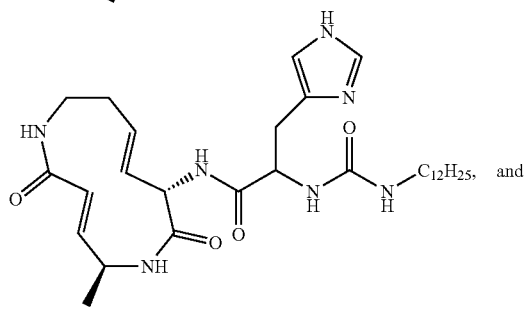

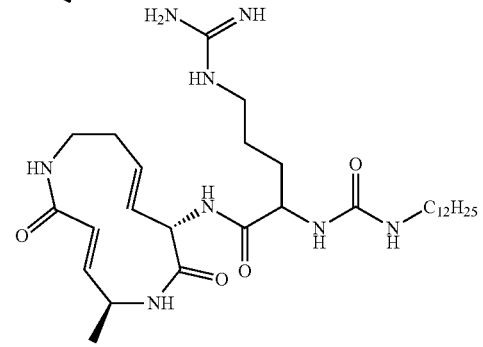

or a pharmaceutically acceptable salt, solvate or prodrug thereof.

In a certain embodiment, the disclosure provides for a compound comprising a structure of Formula II(b):

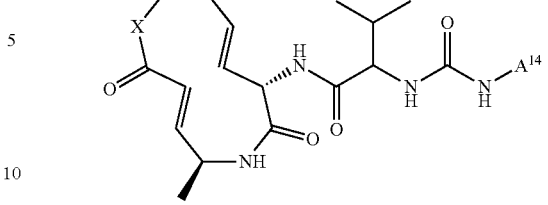

Formula II (b)

or a pharmaceutically acceptable salt, solvate or prodrug thereof, wherein:

X is N, or O;

$A^{14}$ is selected from the group comprising hydrogen, deuterium, FG, optionally substituted $(C_1-C_{16})$alkyl, optionally substituted $(C_1-C_{16})$alkenyl, optionally substituted $(C_1-C_{16})$alkynyl, optionally substituted $(C_1-C_{15})$hetero-alkyl, optionally substituted $(C_1-C_{15})$hetero-alkenyl, optionally substituted $(C_1-C_{15})$hetero-alkynyl, optionally substituted cycloalkyl, optionally substituted aryl, and optionally substituted heterocycle. In a further embodiment, the disclosure provides for a compound having the structure of:

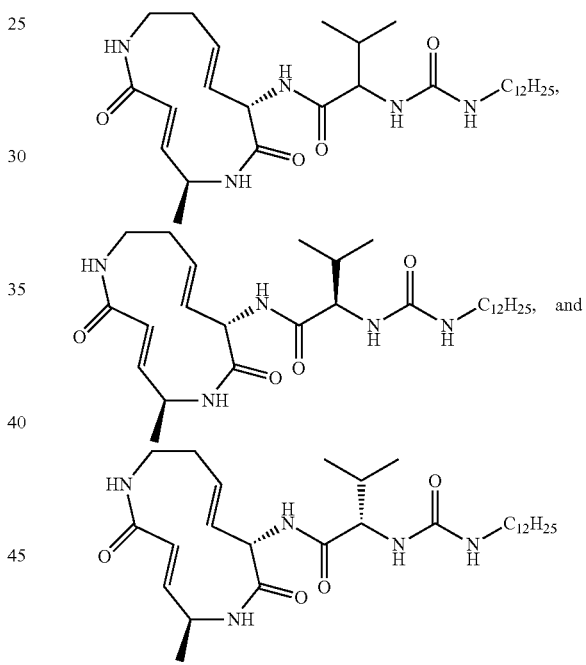

or a pharmaceutically acceptable salt, solvate or prodrug thereof.

In yet a further embodiment, the disclosure provides for a compound having the structure of:

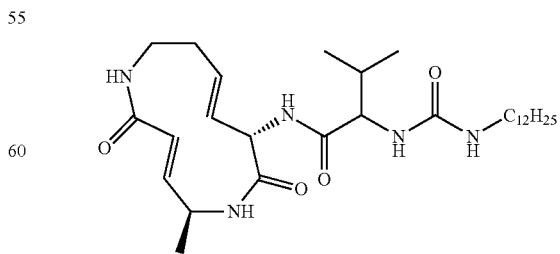

or a pharmaceutically acceptable salt, solvate or prodrug thereof.

In another embodiment, the disclosure provides for a pharmaceutical composition comprising a compound of the disclosure or a pharmaceutical acceptable salt thereof and one or more pharmaceutically acceptable carriers. In yet another embodiment, the pharmaceutical composition is formulated to be delivered intravenously or subcutaneously. In a further embodiment, the pharmaceutical composition disclosed herein is a resuspended in a solution for intravenous or subcutaneous administration and comprises between 1 mg/mL to 5 mg/mL of a compound disclosed herein.

In a particular embodiment, the disclosure provides method of treating a subject having or suspected of having a proteasome mediated disorder comprising administering a compound of the disclosure, or a pharmaceutical composition comprising a compound of the disclosure. In a further embodiment, the proteasome mediated disorder is selected from cancer, nonmalignant tumors, autoimmune diseases, inflammatory related disorders, and disorders that are ameliorated by administering an immunosuppressive agent. Examples of cancer and nonmalignant tumors include, but are not limited to, ovarian cancer, breast cancer, colorectal cancer, colon cancer, renal cancer, rectal cancer, pancreatic cancer, prostate cancer, stomach cancer, gastrointestinal cancer, gastric cancer, esophageal cancer, bile duct cancer, lung tumors, liver tumors, epidermoid tumors, squamous tumors, head and neck tumors, epithelial squamous cell cancer, thyroid cancer, cervical cancer, neuroendocrine tumors, cancer of the peritoneum, hepatocellular cancer, hepatoblastomas, glioblastomas, bladder cancer, hepatomas, endometrial or uterine carcinomas, salivary gland carcinomas, kidney or renal cancer, bone cancer, soft tissue sarcoma, cholangiocarcinoma, gallbladder carcinoma, myeloma, multiple myeloma, vulval cancer, hepatic carcinoma, anal carcinoma, penile carcinoma, hematopoietic cancer, androgen-dependent tumors, androgen-independent tumors, Kaposi's sarcoma, synovial sarcoma, vasoactive intestinal peptide secreting tumor, CNS neoplasms, neuroblastomas, capillary hemangioblastomas, meningiomas, cerebral metastases, melanomas, rhabdomyosarcomas, glioblastomas, medulloblastomas, ependymomas, Wilm's cancer, Ewing's cancer, osteosarcomas, rhabdomyosarcomas, retinoblastomas, adrenal cortical cancer, adrenal cancer, and leiomyosarcomas. In a particular embodiment, the cancer is kidney cancer, myeloma, or multiple myeloma.

In a certain embodiment, the disclosure provides for administering a compound disclosed herein or a pharmaceutical composition comprising a compound of the disclosure in combination with one or more additional therapeutic agents, such as chemotherapeutic agents. Examples of chemotherapeutic agents include, but are not limited to wherein the one or more chemotherapeutic agents is selected from cisplatin, carboplatin, vinblastine, platinum, arginine deiminase, asparaginase, thiotepa, cyclophosphamide, busulfan, improsulfan, piposulfan, calusterone, dromostanolone propionate, epitiostanol, mepitiostane, testolactone, aminoglutethimide, mitotane, trilostane, flutamide, nilutamide, bicalutamide, leuprolide, goserelin, aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, tamoxifen, raloxifene, 4-hydroxytamoxifen, trioxifene, keoxifene, LY 117018, onapristone, toremifene, methotrexate, 5-fluorouracil, denopterin, methotrexate, pteropterin, trimetrexate, benzodopa, carboquone, meturedopa, uredopa, ethylenimines, altretamine, triethylenemelamine, trietylenephosphoramide, triethylenethiophosphaoramide, trimethylolomelamine, frolinic acid, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, paclitaxel, docetaxel, RFS 2000, thymidylate synthase inhibitors, aceglatone, aldophosphamide glycoside, aminolevulinic acid, amsacrine, bestrabucil, bisantrene, edatraxate, defofamine, demecolcine, diaziquone, difluoromethylornithine (DMFO), elformithine, elliptinium acetate, etoglucid, gallium nitrate, hydroxyurea, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, tenuazonic acid, triaziquone, 2,2',2''-trichlorotriethylamine, urethane, vindesine, dacarbazine, mannomustine, mitobronitol, mitolactol, pipobroman, gacyto sine, arabinoside ("Ara-C"), chlorambucil, gemcitabine, 6-thioguanine, mercaptopurine, methotrexate, etoposide, ifosfamide, mitomycin C, mitoxantrone, vincristine, vinorelbine, navelbine, novantrone, teniposide, daunomycin, aminopterin, xeloda, ibandronate, CPT-11, retinoic acid, esperamicins, and capecitabine. In a particular embodiment, the disclosure provides for administering a compound disclosed herein or a pharmaceutical composition comprising a compound of the disclosure in combination with one or more chemotherapeutic agents selected from vinblastine, floxuridine, 5-fluorouracil, capecitabine, gemcitabine, bortezomib, cyclophosphamide, melphalan, doxorubicin, idarubicin, cisplatin, etoposide, and bendamustine.

DESCRIPTION OF DRAWINGS

FIG. 1 presents the structure of a novel and highly potent proteasome inhibitor, TIR-199. For structural comparison purposes, the structures of various proteasome inhibitors are also presented, including glidobactin A, syringolin A, SylaLIP, and bortezomib.

FIG. 3 provides the preliminary results of a dose response study performed with 60 cancerous cell lines and varying $\log_{10}$ amounts of TIR-199. The results demonstrate that TIR-199 suppressed the growth and/or induce apoptosis of the cells in a dose dependent manner. TIR-199 was found to be a surprisingly effective anti-cancer agent, as TIR-199 suppressed the growth and/or induced apoptosis in every cancerous cell line. TIR-199 was also shown to be a relatively potent anti-cancer agent as indicated by the $GI_{50}$, TGI, and $LC_{50}$ values.

Figure 7:
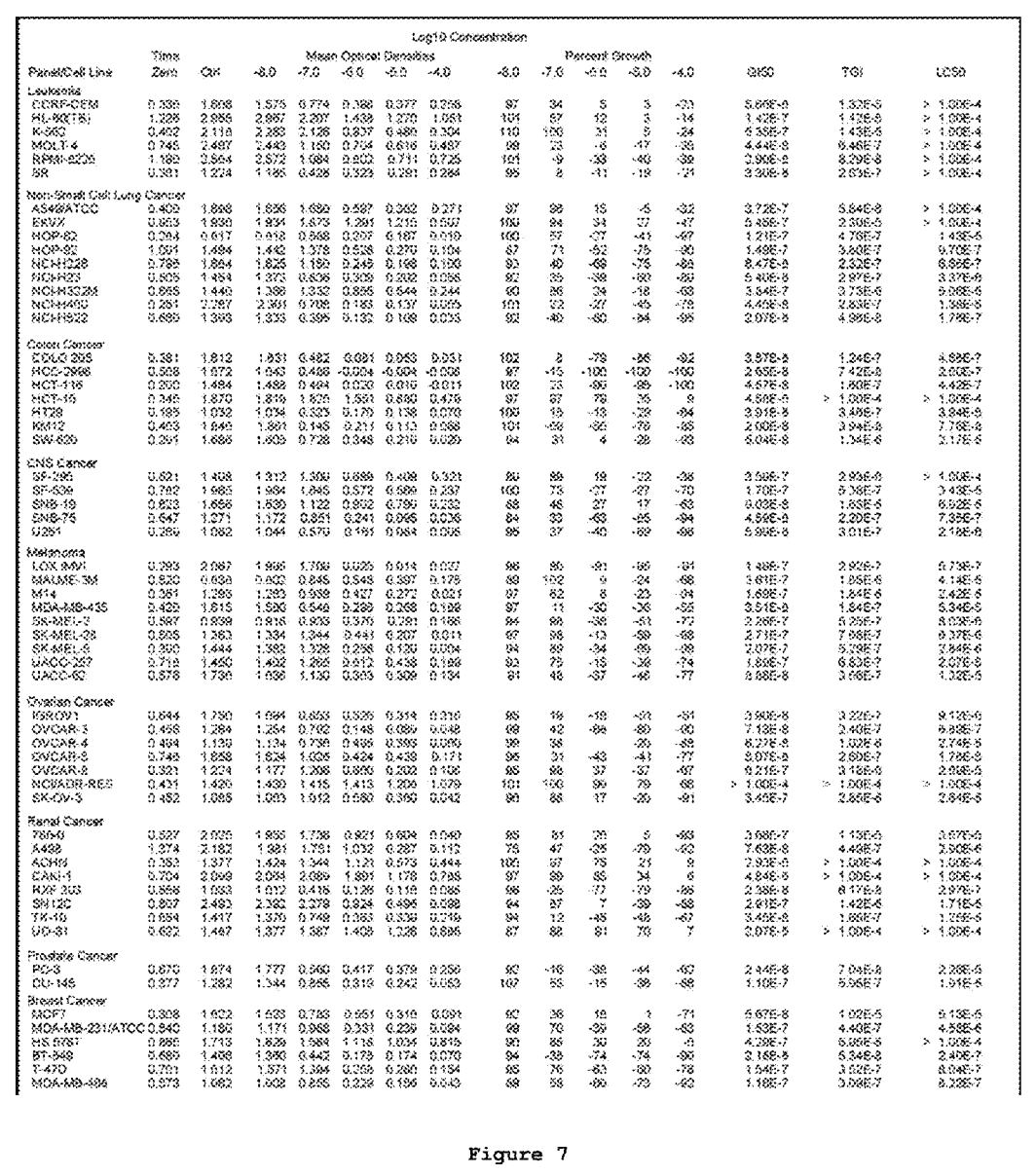

FIG. 7 presents a replicate of the dose response cell line study performed with 60 cancerous cell lines and varying $log_{10}$ amounts of TIR-199. The replicate confirms the results presented in FIG. 3.

Figure 11:
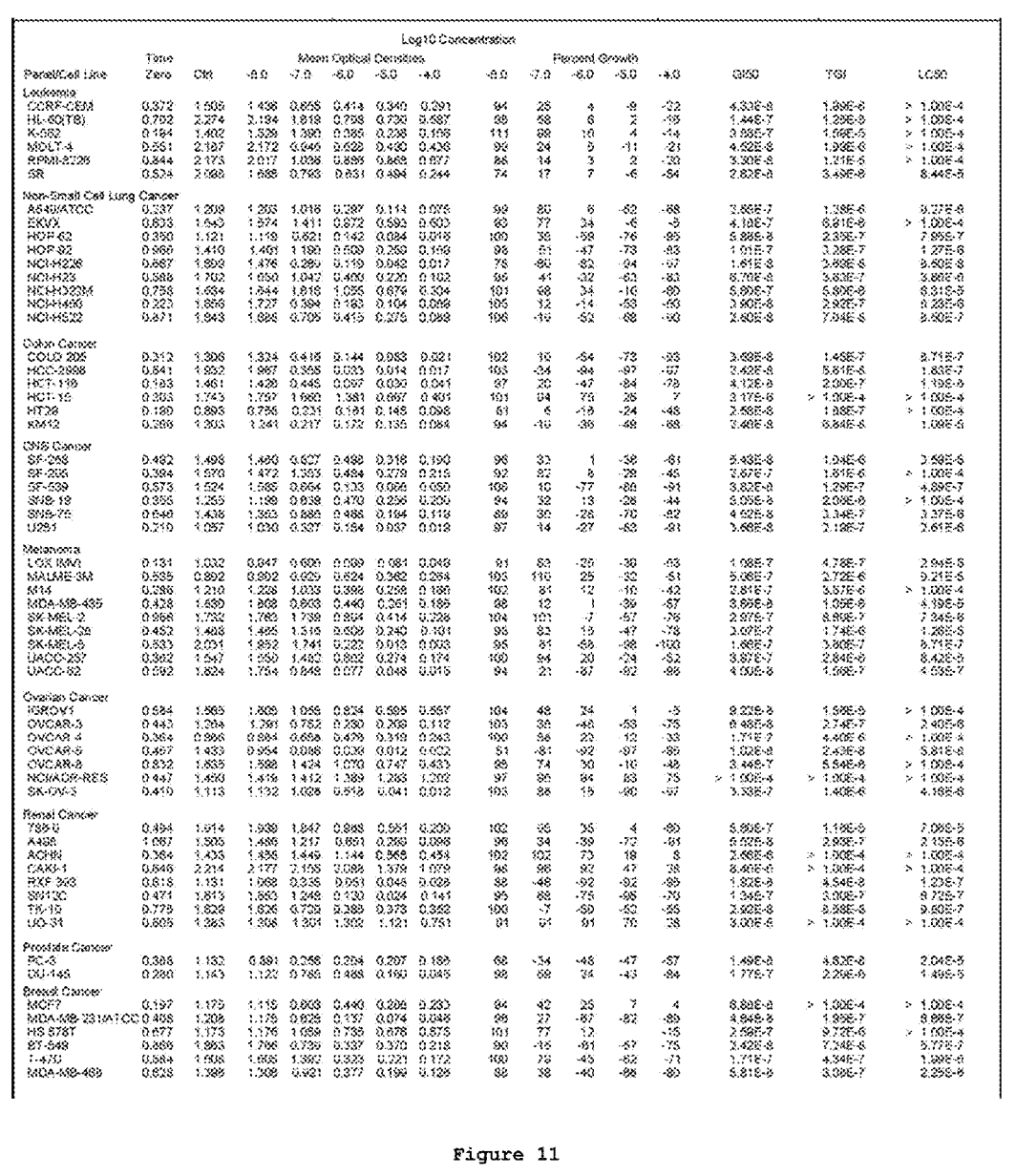

FIG. 11 presents a second replicate of the dose response cell line study performed with 60 cancerous cell lines and varying $log_{10}$ amounts of TIR-199. The second replicate confirms the previous results.

DETAILED DESCRIPTION

Figure 2:
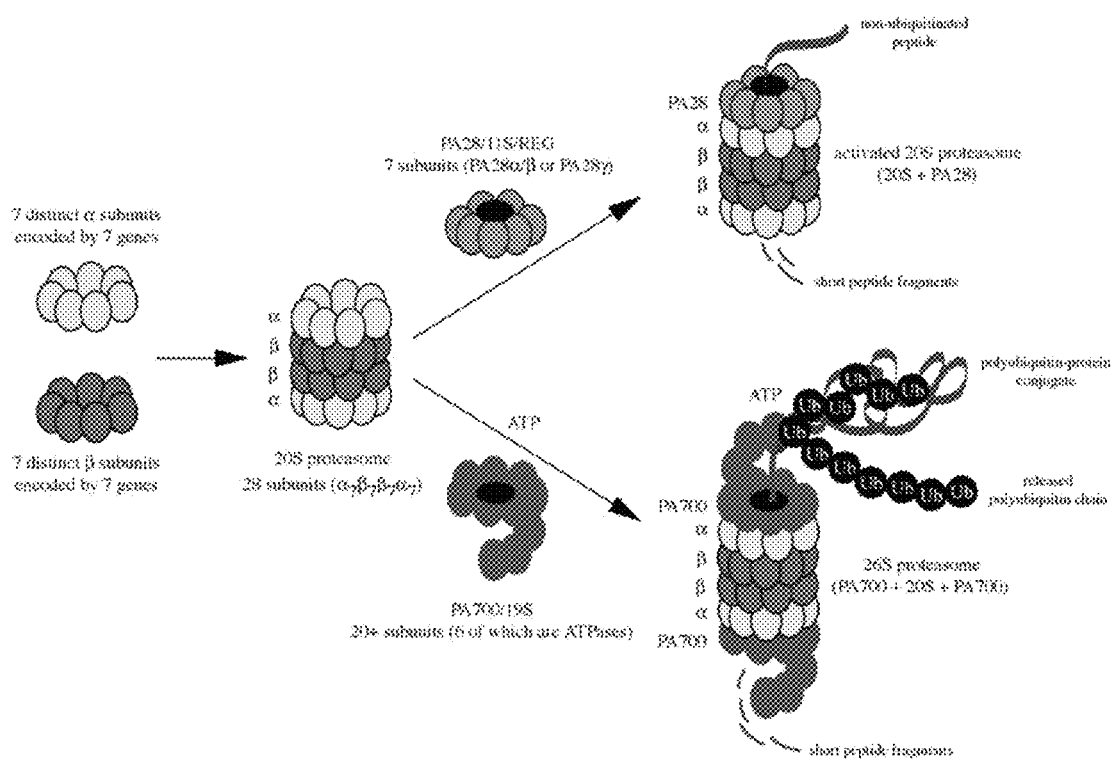
FIG. 2 provides a diagram of the components making up the proteasome, including the assembly of the components into a functioning proteasome.
Figure 4:
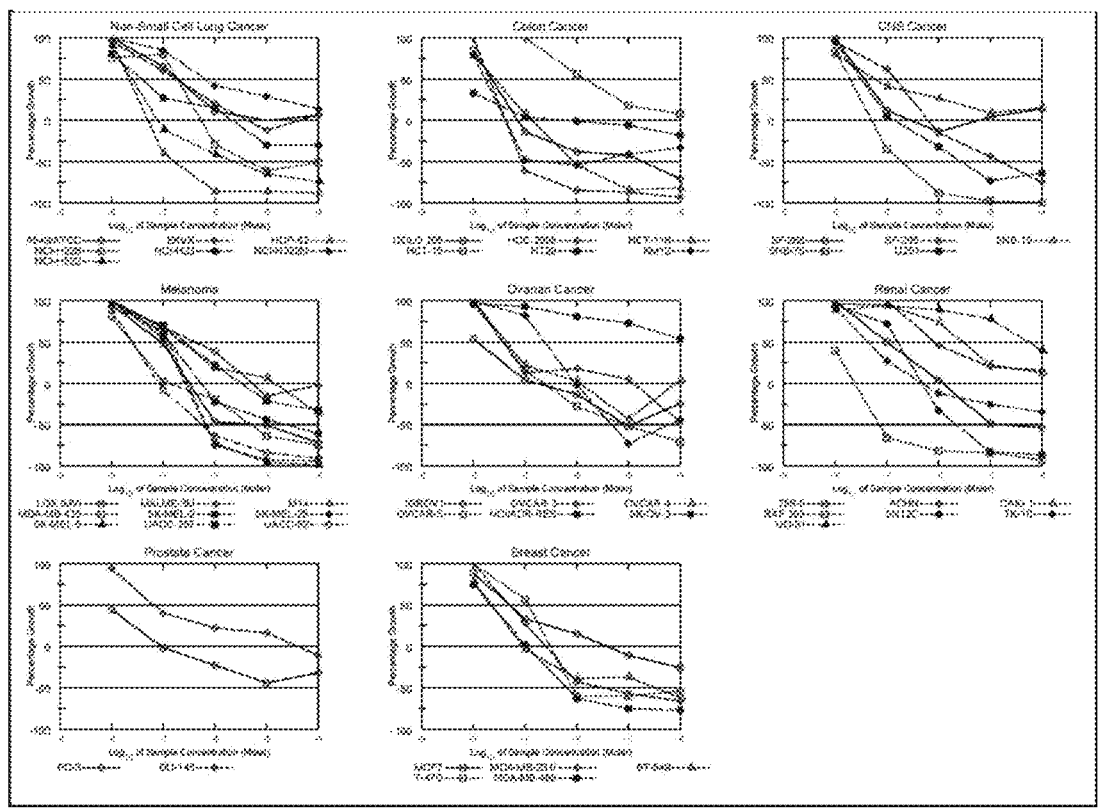
FIG. 4 provides dose-response curves based upon the preliminary results presented in FIG. 3. The curves are grouped according to the type of cancer in which the cell line was isolated from. Dose response-curves for non-small cell lung cancers, colon cancers, CNS cancers, melanomas, ovarian cancers, renal cancers, prostate cancers, and breast cancers are presented.
Figure 5:
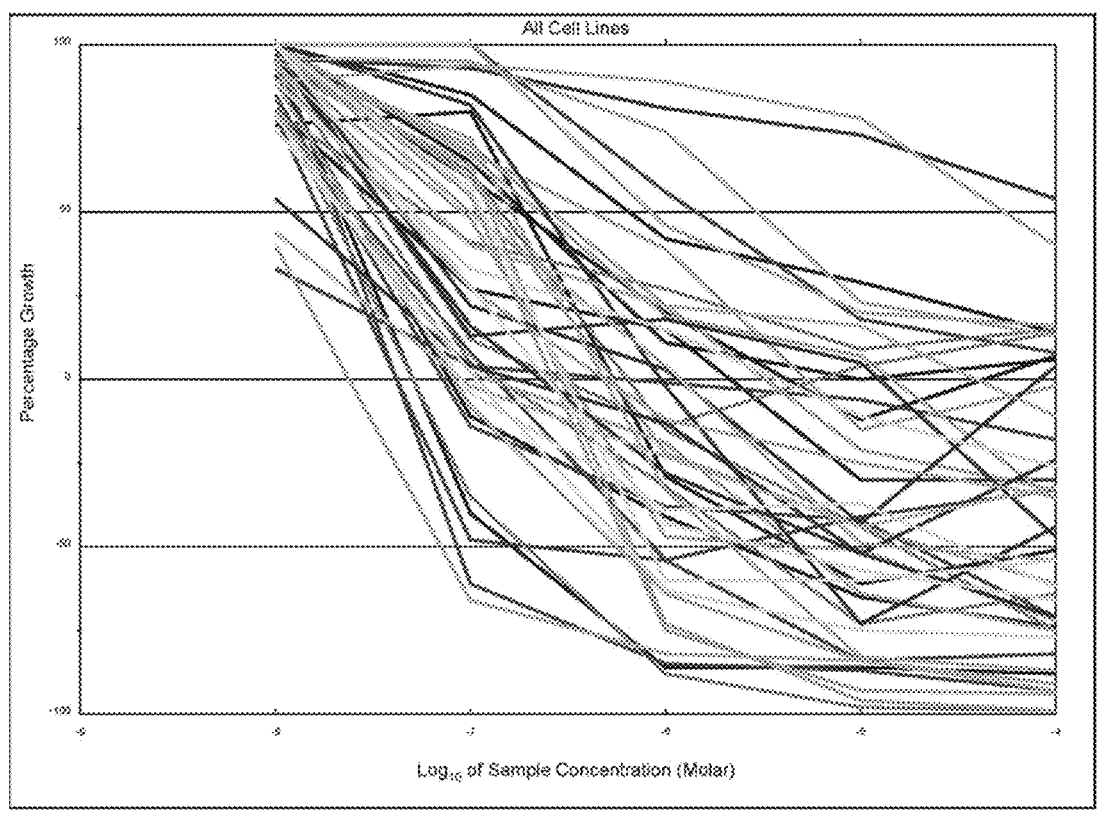
FIG. 5 provides the dose-response curves of FIG. 4 in a single graph.
Figure 6:
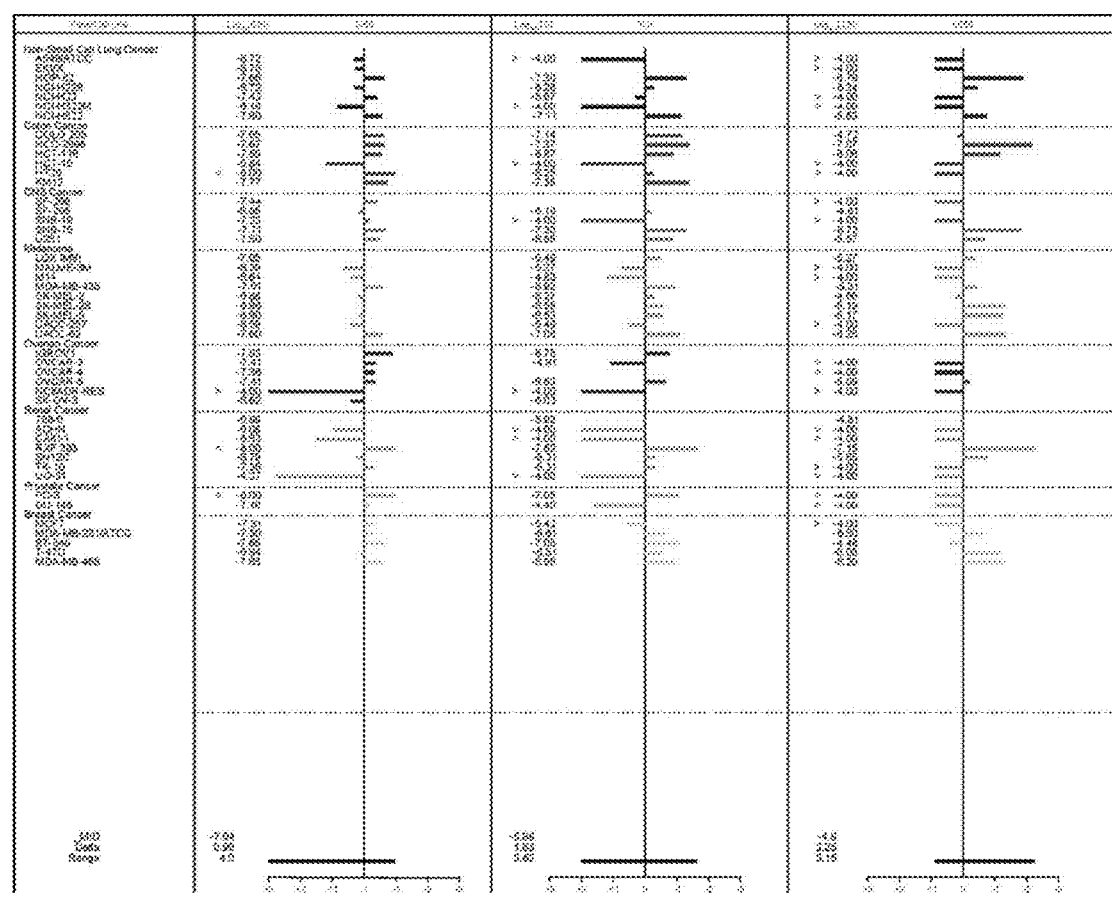
FIG. 6 presents a comparison between the $GI_{50}$, TGI, and $LC_{50}$ and a $Log_{10}$ dose of TIR-199 from the raw numbers of FIG. 4 for each of the tested cancerous cell lines.
Figure 8:
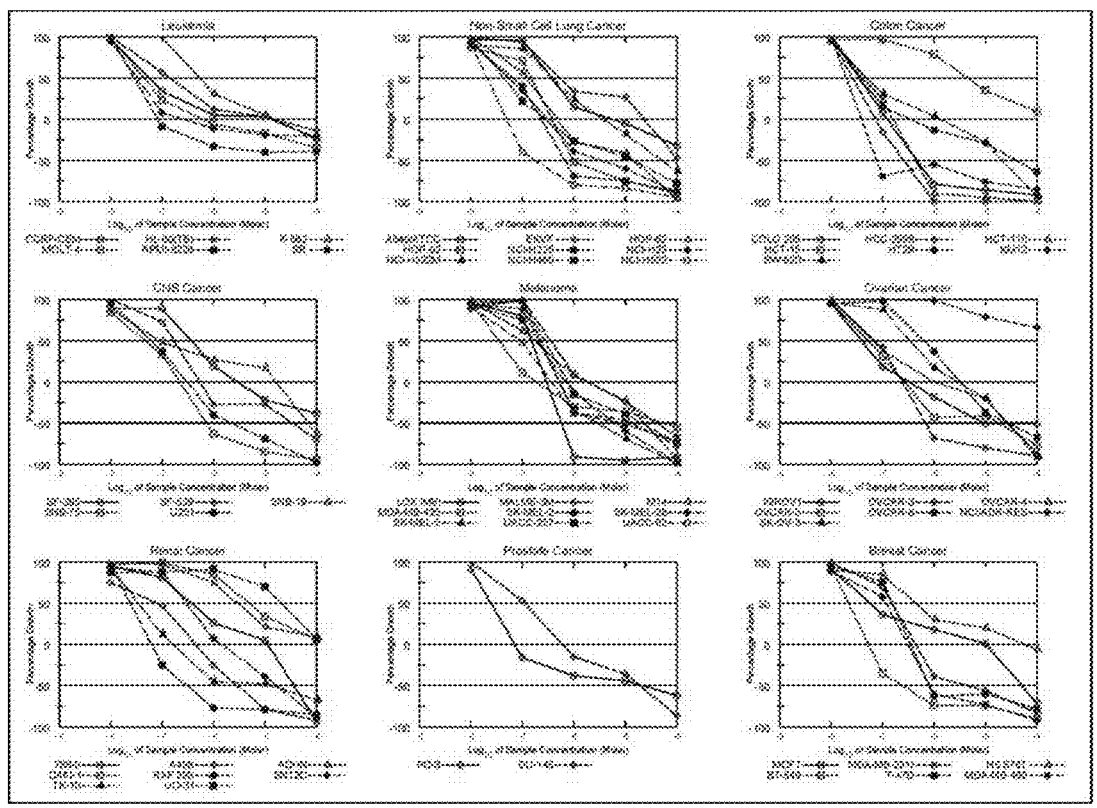
FIG. 8 provides dose-response curves based upon the raw number results presented in FIG. 7. The curves are grouped according to the type of cancer in which the cell line was isolated from. Dose-response curves for non-small cell lung cancers, colon cancers, CNS cancers, melanomas, ovarian cancers, renal cancers, prostate cancers, and breast cancers are presented.
Figure 9:
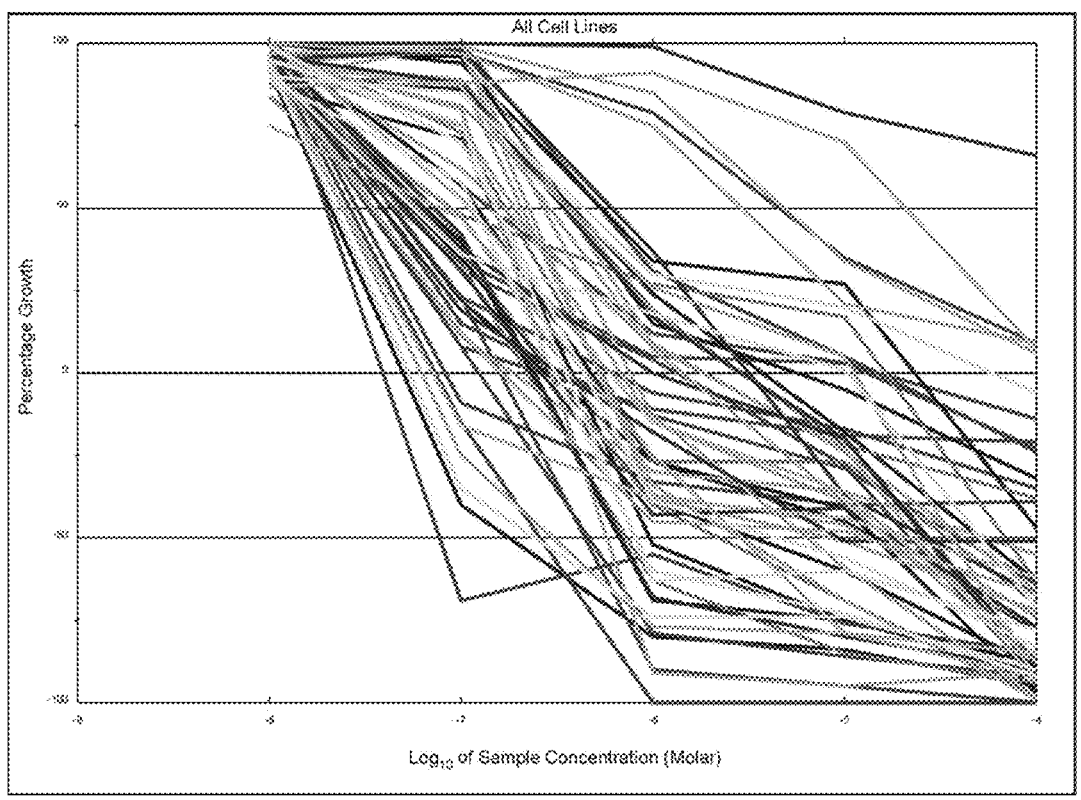
FIG. 9 provides the dose-response curves of FIG. 8 in a single graph.
Figure 10:
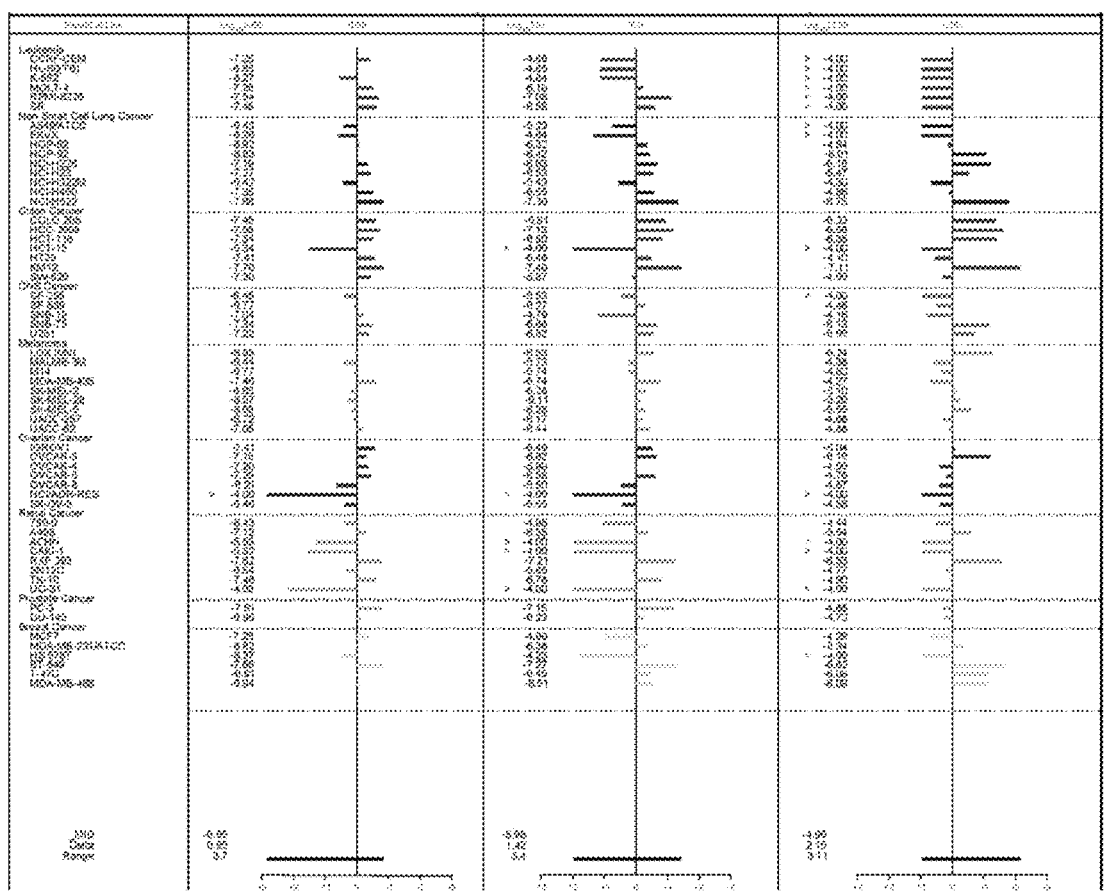
FIG. 10 presents a comparison between the $GI_{50}$, TGI, and $LC_{50}$ and a $Log_{10}$ dose of TIR-199 from the raw numbers of FIG. 7 for each of the tested cancerous cell lines.
Figure 12:
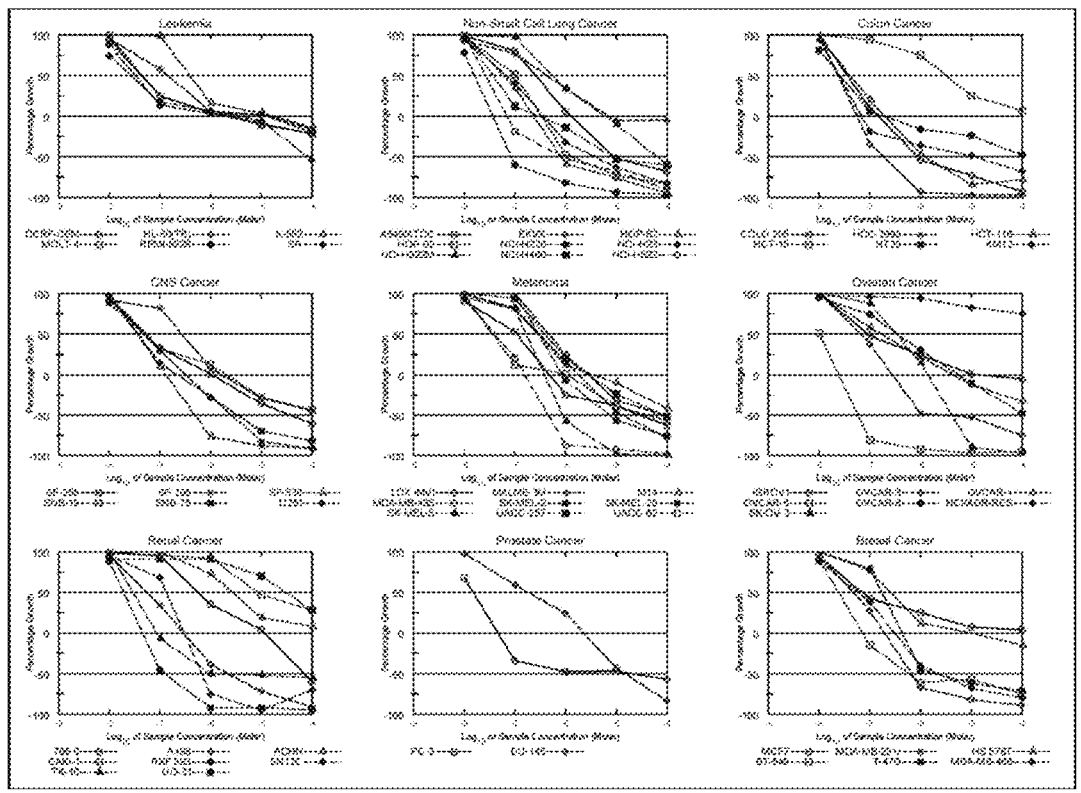
FIG. 12 provides dose-response curves based upon the raw number results presented in FIG. 11. The curves are grouped according to the type of cancer in which the cell line was isolated from. Dose-response curves for non-small cell lung cancers, colon cancers, CNS cancers, melanomas, ovarian cancers, renal cancers, prostate cancers, and breast cancers are presented.
Figure 13:
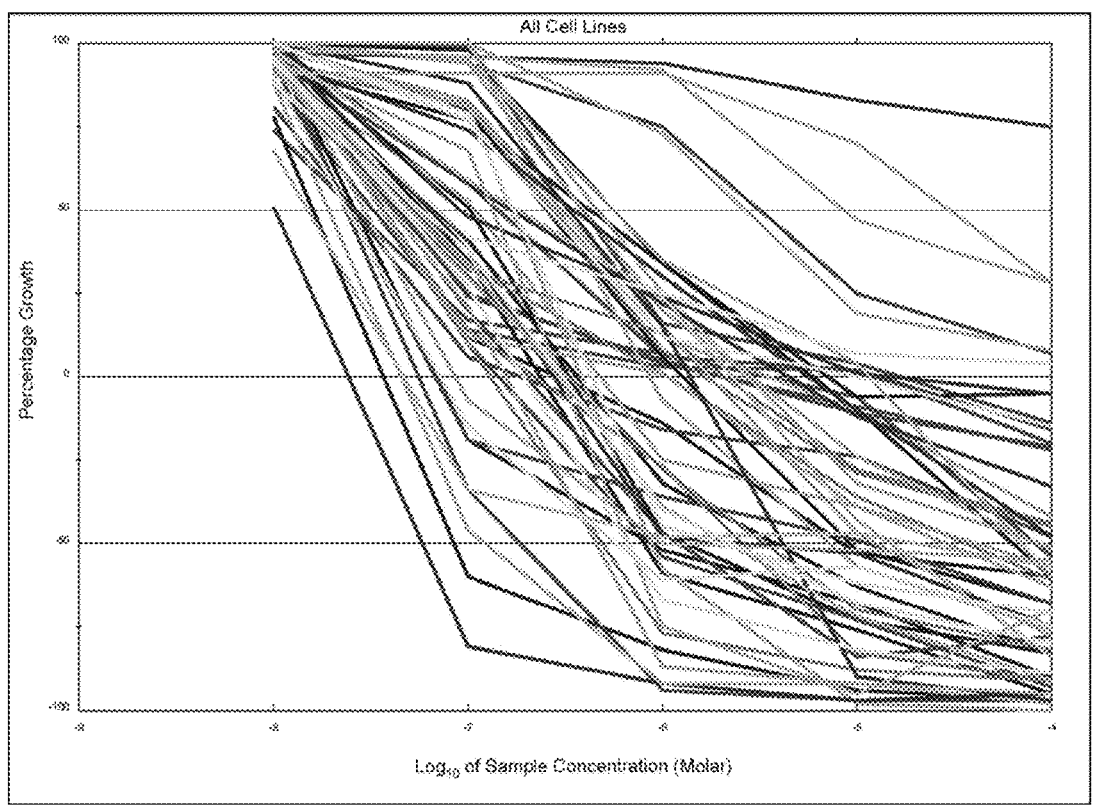
FIG. 13 provides the dose-response curves of FIG. 12 in a single graph.
Figure 14:
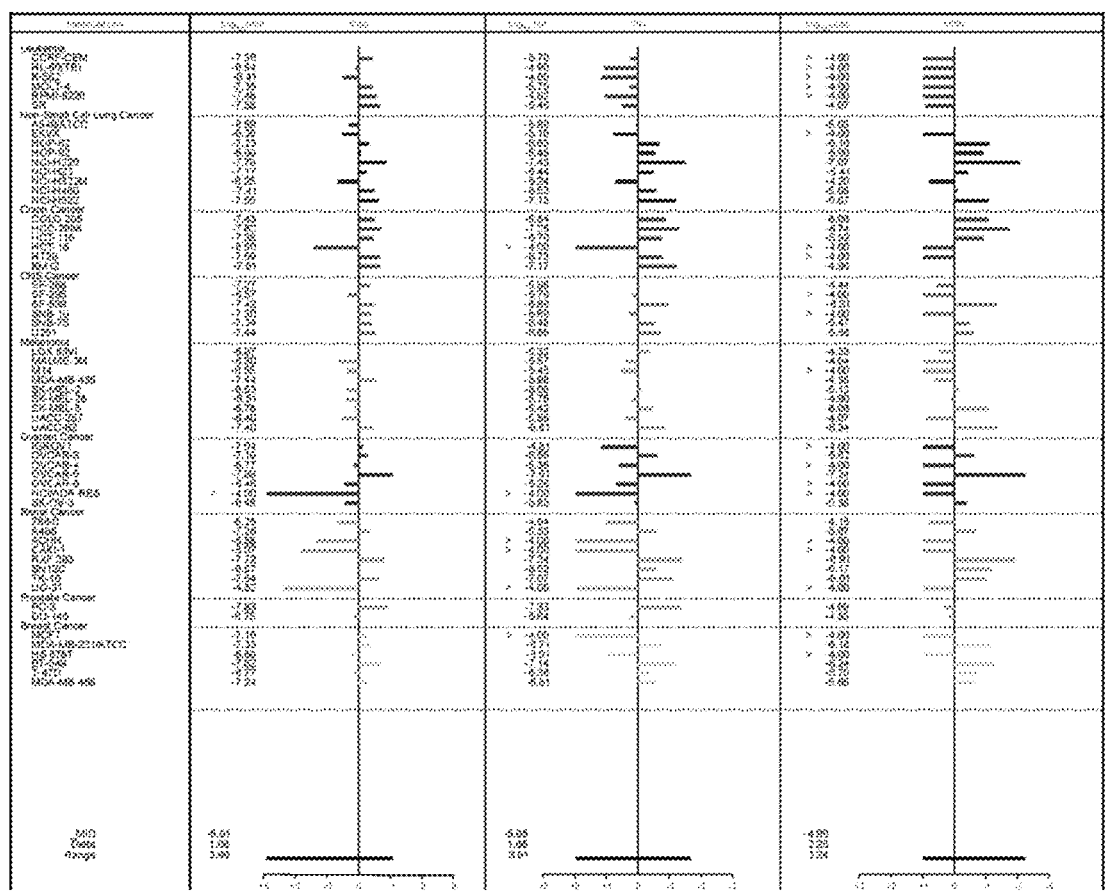
FIG. 14 presents a comparison between the $GI_{50}$, TGI, and $LC_{50}$ and a $Log_{10}$ dose of TIR-199 from the raw numbers of FIG. 11 for each of the tested cancerous cell lines.

As used herein and in the appended claims, the singular forms "a," "and," and "the" include plural referents unless the context clearly dictates otherwise. Thus, for example, reference to "a proteasome" includes a plurality of such proteasomes and reference to "the anti-cancer agent" includes reference to one or more anti-cancer agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although there are many methods and reagents similar to or equivalent to those described herein, the exemplary methods and materials are presented herein.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this invention, a substituent would include deuterium atoms.

The term "hydrocarbons" refers to groups of atoms that contain only carbon and hydrogen. Examples of hydrocarbons of the disclosure include, but are not limited to, alkanes, alkenes, alkynes, arenes, and benzyls.

The term "functional group" or "FG," as used herein, refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by additional nearby functional groups. The atoms of functional groups are linked to each other and to the rest of the molecule by covalent bonds. Examples of "functional group" or "FG" of the disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "heterocycle," as used herein, refers to ring structures that contain at least 1 noncarbon ring atom. A "heterocycle" for the purposes of this disclosure encompass from 1 to 7 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The term "hetero-" when used as a prefix, such as, heteroalkyl, hetero-alkenyl, hetero-alkynyl, or hetero-hydrocarbon, for the purpose of this disclosure refers to the specified hydrocarbon having one or more carbon atoms replaced by noncarbon atoms as part of the parent chain. Examples of such noncarbon atoms include, but are not limited to, N, O, S, Si, Al, B, and P. If there is more than one noncarbon atom in the hetero-hydrocarbon chain then this atom may be the same element or may be a combination of different elements, such as N and O.

The term "hydroxyl protecting group," as used herein, refers to a group that can reversible bind to a hydroxyl so as to prevent the hydroxyl from participating in an unwanted chemical reaction. The hydroxyl protecting group may be removed under certain reaction conditions so as to provide a free hydroxyl. Examples of "hydroxyl protecting groups" include, but are not limited to:

(a) methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis(2-chloroethoxy)methyl, 2-(trimethylsilyl)ethoxymethyl, menthoxymethyl, 1-ethoxyethyl, 1-(2-chloroethoxyl)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl and the like;

(b) benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4-acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl(trityl), α-naphthyldiphenylmethyl, (4-methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,i]fluorenylmethyl)-4,4'-dimethoxytrityl, 9-anthryl, 9-(9-phenyl)xanthenyl, 9-(9-phenyl-10-oxo)anthryl and the like;

(c) trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris(trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

(d) —C(O)$R^{80}$, where $R^{80}$ is selected from the group consisting of alkyl, substituted alkyl, aryl and more specifically $R^{80}$ is hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis(4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, .alpha.-naphthyl, benzoyl and the like;

(e) —C(O)O$R^{80}$, where $R^{80}$ is selected from the group consisting of alkyl, substituted alkyl, aryl and more specifically $R^{80}$ is methyl, methoxymethyl, 9-fluorenylmethyl, ethyl, 2,2,2-trichloroethyl, 1,1-dimethyl-2,2,2-trichloroethyl, 2-(trimethylsilyl)ethyl, 2-(phenylsulfonyl)ethyl, isobutyl, tert-butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The term "amine protecting group," as used herein, refers to a group that can reversible bind to an amine so as to prevent the amine from participating in an unwanted chemical reaction. The amine protecting group may be removed under certain reaction conditions so as to provide a free amine. Examples of "amine protecting groups" include, but are not limited to:

(a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonytmethyl, m-nitrophenyl, 3,5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzene-sulfonyl, N-2,6-dimethyl-4-methoxybenzenesulfonyl, N-pentamethylbenzenesulfonyl, N-2,3,5,6-tetramethyl-4-methoxybenzenesulfonyl and the like;

(b) —C(O)OR$^{80}$, where R$^{80}$ is selected from the group consisting of alkyl, substituted alkyl, aryl and more specifically R$^{80}$ is a methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, vinyl, allyl, 1-isopropylallyl, cinnamyl, 4-nitrocinnamyl, 3-(3-pyridyl)prop-2-enyl, 8-quinolyl, N-hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

A bond indicated by a straight line and a dashed line indicates a bond that may be a single covalent bond or alternatively a double covalent bond. However, in the case where an R group defines an atom that is connected to another atom by a straight line and a dashed line which would exceed its maximum valence if the bond was a double covalent bond then the bond would only be a single covalent bond. For example, where R can be hydrogen and is connected to another atom by a straight line and a dashed line, then hydrogen would only form a single bond even though such a bond is indicated as being a single or double bond.

The term "pharmaceutically acceptable carrier," "pharmaceutically acceptable excipient," "physiologically acceptable carrier," or "physiologically acceptable excipient" as used herein, refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. Examples of "pharmaceutically acceptable carriers" and "pharmaceutically acceptable excipients" can be found in the following, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004.

The terms "active ingredient," "active compound," and "active substance" as used herein, refers to a compound that when administered, alone or in combination with one or more pharmaceutically acceptable excipients or carriers, exerts or induces a physiological effect in a subject. Generally, an active ingredient can be administered to a subject to treat, prevent, or ameliorate one or more symptoms of a disease or disorder.

The terms "drug," or "therapeutic agent," as used herein, refers to a compound, or a pharmaceutical composition thereof, which is administered to a subject to treat, prevent, or ameliorate one or more symptoms of a disease or disorder.

The term "chemotherapeutic agent" as used herein, refers to any chemical used to treat cancer and/or a neoplastic disorder.

The term "release controlling excipient" as used herein, refers to an excipient whose primary function is to modify the duration or place of release of the active substance from a dosage form as compared with a conventional immediate release dosage form.

The term "nonrelease controlling excipient" as used herein, refers to an excipient whose primary function do not include modifying the duration or place of release of the active substance from a dosage form as compared with a conventional immediate release dosage form.

The terms "treat", "treating" and "treatment", as used herein, refers to ameliorating symptoms associated with a disease or disorder (e.g., kidney cancer), including preventing or delaying the onset of the disease or disorder symptoms, and/or lessening the severity or frequency of symptoms of the disease or disorder.

The term "subject" as used herein, refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein. For example, a mammalian subject can refer to a human patient.

The term "disorder" as used herein is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

For purposes of the disclosure, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer.

Proteasome is the main multi-protein complex involved in degrading protein in a cell (e.g., see FIG. 2). The proteasome also plays a role in regulating biological signaling processes involving NF-κB. For many cancers, constitutive NF-κB activity protects the cancer cells from undergoing apoptosis. Certain cancers (e.g., multiple myeloma and kidney cancer) are highly dependent on NF-κB signaling. By disrupting the regulated activation of pro-growth cell cycle proteins, like NF-κB, proteasome inhibitors have been found to be effective anti-tumor agents by inducing apoptosis in malignant cells.

The vertebrate immune system is dependent on NF-κB signaling. Accordingly, proteasome inhibitors could also be administered as immunomodulators, to suppress or regulate unwanted immune activity, such as treating autoimmune diseases or preventing tissue rejection.

It has been found that some infectious agents (e.g., *M. tuberculosis* and *Plasmodium falciparum*) have proteasomes that are susceptible to differential inhibition compared to the host proteasome. Administering proteasome inhibitors might also be useful as agents to prevent the growth and/or induce apoptosis in invertebrate pathogens/organisms.

Recently, the first therapeutic based on inhibiting the proteasome has been approved by the United States Federal Drug Administration ("FDA") to treat refractory multiple myeloma. This proteasome inhibitor drug, Velcade® (bortezomib), is being examined in combination chemotherapy for cancer in over 400 clinical trials. The administration of bortezomib in humans, however, has been associated with serious side effects, including, increased incidence of peripheral neuropathy, myelosuppression, shingles, gastrointestinal effects and asthenia. These major side effects have limited the utility of bortezomib for treating additional indications outside of relapsed multiple myeloma.

Other known proteasome inhibitors known in the art include natural products from syringolin, glidobactin and cepafungin families. All of these natural products irreversibly inhibit the proteasome, and share similar biosynthetic pathways.

The disclosure provides for compounds disclosed herein that are structurally related to the syringolins. Syringolins are a class of virulence factors compounds which are produced by phytopathogenic bacterium. Studies with syringolins demonstrated that these compounds could irreversibly inhibit eukaryotic proteasomes. Additional studies demonstrated that the proteasome inhibitory effect by syringolins was fairly weak in comparison to other known proteasome inhibitors, such as bortezomib. However, syringolin A derivatives, such as Syla-LIP, have been made that display much higher potency than the syringolin A parent compound.

The disclosure also provides for compounds disclosed herein that are structurally related to glidobactins. Glidobactins are a family of structurally related cytotoxic compounds that were isolated from the soil bacterial strain K481-B101. Glidobactins are acylated tripeptide derivatives that contain a 12-membered ring structure consisting of the two unique non-proteinogenic amino acids erythro-4-hydroxy-1-lysine and 4(S)-amino-2(E)-pentenoic acid. Glidobactins were shown to have anti-tumor activity in a mouse model.

Glidobactin while being similarly effective at inhibiting the proteasome as bortezomib, has a much more complex macrocyclic structure. This larger more complex structure has the potential of generating more efficacious therapies by providing more possibilities for medicinal and/or computational chemistry to exploit. Synthetically making glidobactin and glidobactin-based analogs, however, has proved difficult due to glidobactin's complex macrocyclic core structure.

This disclosure provides methods that allow for the facile synthesis of the macrocyclic core structure of glidobactins and glidobactin-based analogs. Medicinal chemistry and computational chemistry can then be utilized to fullest extent to make structural changes to the macrocyclic core structure, as well as, to the attached functional groups.

The disclosure, therefore, provides for a large number of novel compounds that readily incorporate structural variations of the macrocyclic core structure of glidobactin. Compounds based on the macrocyclic core structure of glidobactin would be valuable, in order to (1) develop novel therapeutics; (2) better understand plant host-pathogen interactions; and (3) elucidate fundamental questions concerning the structure and function of the proteasome in diverse eukaryotes, including higher plants and mycobacteria.

Known methods to synthesize of glidobactin A are quite lengthy and produce glidobactin A in low yields. The methods presented herein allow for the controlled synthesis of glidobactin in relatively few steps. The reactions disclosed herein are modular and allow for structural variations to be incorporated at nearly every reaction step. Furthermore, the disclosed methods not only allow for the production of glidobactin, but analogs of glidobactin. Such glidobactin-based analogs, include, but are not limited to, structural substitutions, additions, or eliminations of various functional groups attached to the glidobactin macrocyclic core structure. Moreover, the disclosed methods enable the production of compounds resulting from modifying the glidobactin macrocyclic core structure.

The disclosure provides novel synthetic methods to produce or make the macrocyclic core structure of glidobactin. In one embodiment, the novel synthetic methods presented herein allow for a controlled and a modular based synthesis of the compounds of the disclosure.

In a particular embodiment, a scheme to synthesize a macrocyclic intermediate is presented in Scheme I:

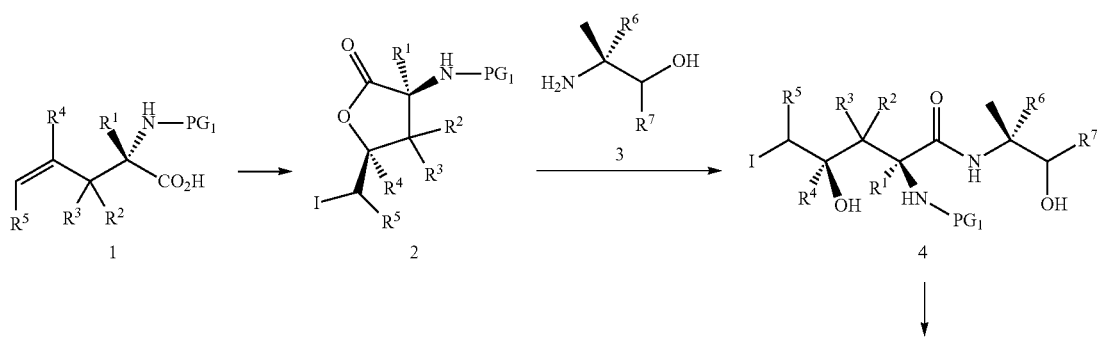

-continued

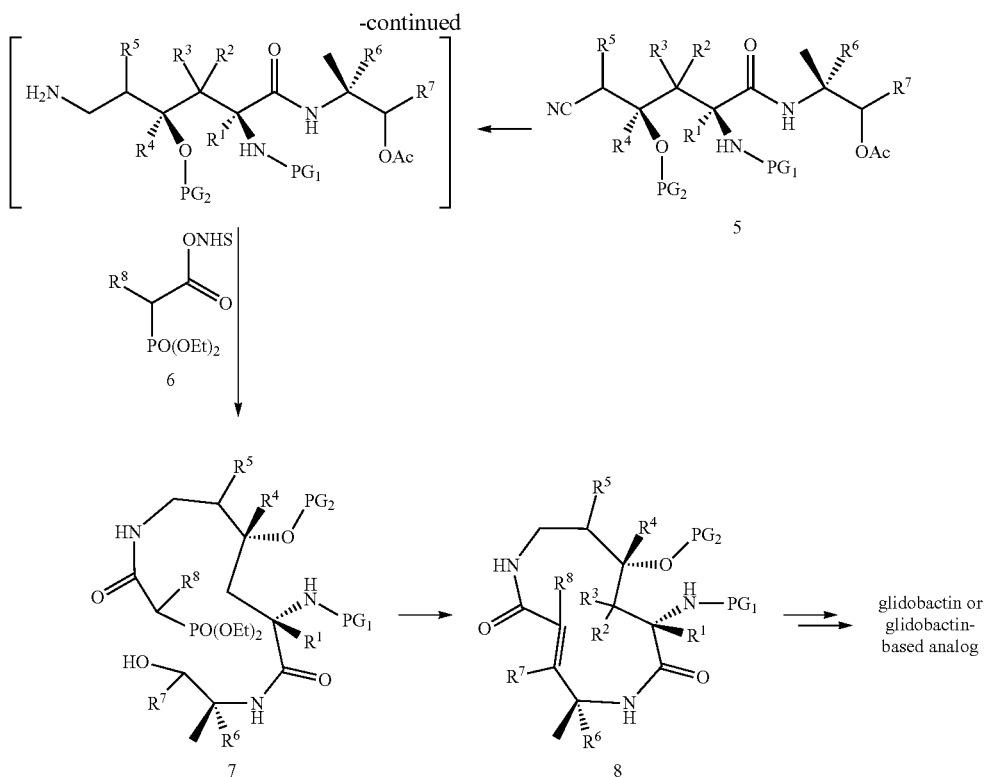

Alkene 1 (wherein "$PG_1$" is an appropriate amine protecting group) is cyclized by reacting with a molecular halide, such as iodine or bromine, in the presence of an appropriate base, such as sodium bicarbonate, to afford lactone 2. Lactone 2 is reacted with amine 3 in an appropriate solvent, such as dichloromethane, to form amide 4 by aminolysis. Amide 4 is first reacted with sodium cyanide, followed by selectively acylating the primary alcohol and protecting the secondary alcohol with an appropriate hydroxyl protecting group ("$PG_2$"), such as methoxymethyl ether, to give cyano-compound 5. Cyano-compound 5 is first reduced in the presence of an appropriate catalyst, such as Raney nickel, in the presence of an appropriate reducing agent, such as hydrogen gas, to give an amino-compound, which is then acylated with phosphonoacetic acid active ester 6 to afford compound 7. Compound 7 undergoes ring closure using Horner-Wadsworth-Emmons reaction conditions to give the glidobactin macrocyclic core structure 8. An additional four-step reaction sequence can then be used to synthesize glidobactin or a glidobactin-based analog from the glidobactin macrocyclic core structure 8.

In addition, Scheme I can be modified to generate macrocyclic intermediates having various ring sizes by adjusting the carbon length of alkene 1 and/or amine 3. For example, alkene 1 may have varying numbers of optionally substituted carbons before the terminal alkene bond, such that lactone 2 is a β-lactone, γ-lactone, δ-lactone, etc.; and amine 3 may have two or more methylene carbons before the terminal hydroxyl containing carbon.

In a particular embodiment, a method to make a compound disclosed herein provides for macrocyclic intermediate having a structure of Formula I:

Formula I

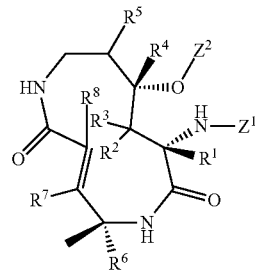

wherein, $R^1$-$R^3$, and $R^6$-$R^8$ are individually selected from the group comprising hydrogen, deuterium, hydroxyl, halo, cyano, amino, nitro, ether, ester, optionally substituted ($C_1$-$C_6$)alkyl, optionally substituted ($C_1$-$C_6$)alkenyl, optionally substituted ($C_1$-$C_6$)alkynyl, optionally substituted ($C_1$-$C_5$)hetero-alkyl, optionally substituted ($C_1$-$C_5$)hetero-alkenyl, and optionally substituted ($C_1$-$C_5$)hetero-alkynyl;

$R^4$-$R^5$ are individually selected from the group comprising hydrogen, deuterium, hydroxyl, halo, cyano, amino, nitro, ether, ester, optionally substituted ($C_1$-$C_6$)alkyl, optionally substituted ($C_1$-$C_6$)alkenyl, optionally substituted ($C_1$-$C_6$) alkynyl, optionally substituted ($C_1$-$C_5$)hetero-alkyl, optionally substituted ($C_1$-$C_5$)hetero-alkenyl, optionally substituted ($C_1$-$C_5$)hetero-alkynyl, and wherein $R^4$ may be linked to $R^5$ so as to form an optionally substituted ring selected from group comprising cycloalkyl, aryl, and heterocycle;

$Z^1$ is an amine protecting group, hydrogen or deuterium; and $Z^2$ is a hydroxyl protecting group, hydrogen, or deuterium.

In a certain embodiment, a method to make a compound disclosed herein provides for macrocyclic intermediate having a structure of Formula I(a):

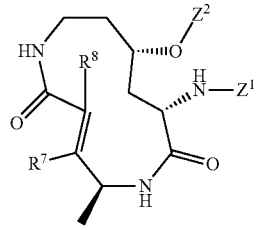

Formula I(a)

wherein, $R^7$-$R^8$ are individually selected from the group comprising hydrogen, deuterium, hydroxyl, halo, cyano, amino, nitro, ether, ester, optionally substituted ($C_1$-$C_3$)alkyl, optionally substituted ($C_1$-$C_3$)alkenyl, and optionally substituted ($C_1$-$C_3$)alkynyl;

$Z^1$ is an amine protecting group, hydrogen or deuterium; and $Z^2$ is a hydroxyl protecting group, hydrogen, or deuterium.

In a further embodiment, a method to make a compound disclosed herein provides for macrocyclic intermediate having a structure of Formula I(b):

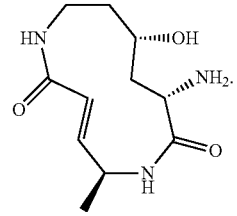

Formula I(b)

The disclosure provides for compounds that can be used as proteasome inhibitors. In a certain embodiment, the disclosure provides for compounds which have proteasome inhibiting activities comparable to bortezomib. In another embodiment, the compounds disclosed herein can be used to selectively inhibit proteasomes of non-vertebrate organisms. In a further embodiment, the compounds disclosed herein can be used as anti-cancer and/or anti-tumor agents. In yet a further embodiment, the compounds disclosed herein can be used as immunemodulators.

In a particular embodiment, a reaction scheme to synthesize compounds of the disclosure is presented in Scheme II:

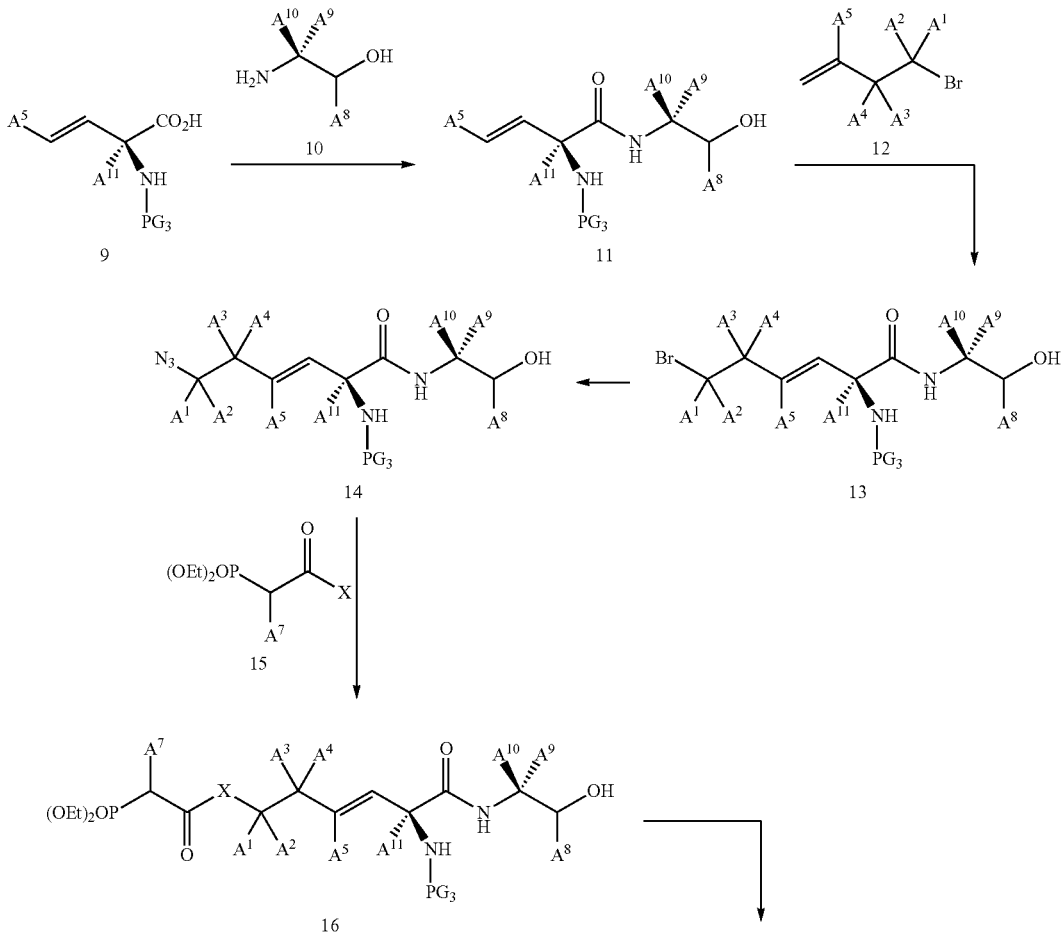

Scheme II

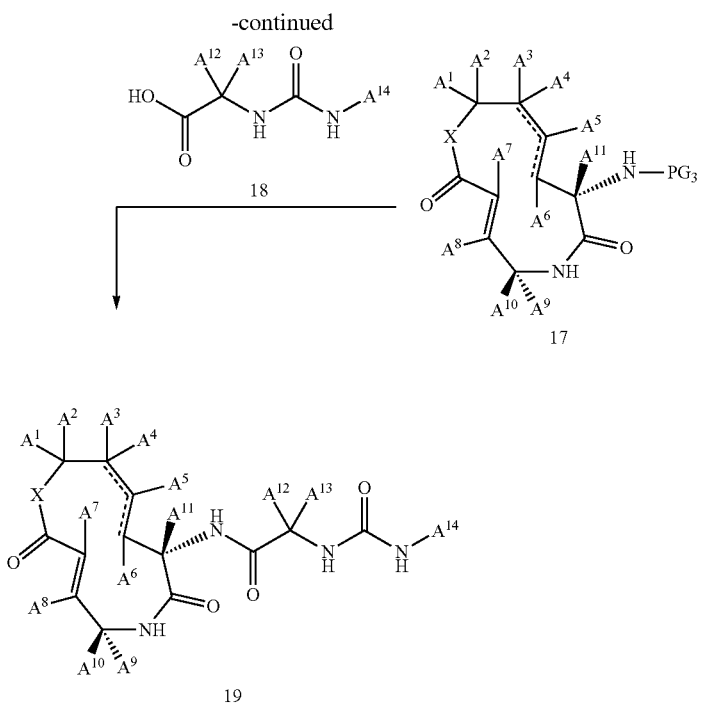

Various modular intermediates, including amine 10, bromo-alkene 12, phosphodiester 15 (wherein X is either an oxygen, nitrogen, or sulfur containing group), and carbamide 18 can be purchased commercially, or made by using standard chemical reactions known in the art.

Carboxylic acid 9 (wherein $PG_3$ is an appropriate amine protecting group) is available in three steps from commercially available (Z)-Met-OMe. Carboxylic acid 9 is coupled with amine 10 in the presence of an appropriate coupling agent, such as mixed anhydrides or 2-isobutoxy-1-isobutoxycarbonyl-1,2-dihydroquinoline, under microwave irradiation to afford amide 11. Commercially available 1-bromo-3-butene 12 undergoes cross-metathesis with amide 11 in the presence of an appropriate catalyst, such as Grubbs second-generation catalyst, in an appropriate solvent, such as dichloromethane, at an elevated temperature to give (E)-1-bromo 13. (E)-1-bromo 13 is reacted with sodium azide in an appropriate solvent, such as dimethylformamide, to give (E)-1-azide 14. (E)-1-azide 14 is reduced with an appropriate reducing agent, such as phosphine or phosphite, to afford an amine intermediate which is then coupled with phosphonoacetic acid active ester 15 in an appropriate solvent, such as dichloromethane, to afford a pre-cyclization intermediate 16. Pre-cyclization intermediate 16 is first oxidized to an aldehyde in the presence of an appropriate oxidizing agent, such as Dess-Martin periodinane, and then cyclized using appropriate Horner-Wadsworth-Emmons reaction conditions, such as $Zn(OTf)_2$/tetramethylenediamine/triethylamine, to form macrocycle intermediate 17. Macrocycle intermediate 17 is first de-protected under appropriate conditions and then coupled to carbamate 18 under peptide coupling conditions, such as the use of carbodiimides and triazoles, to afford a compound 19.

In a particular embodiment, the disclosure provides for one or more compounds comprising a structure of Formula II:

Formula II

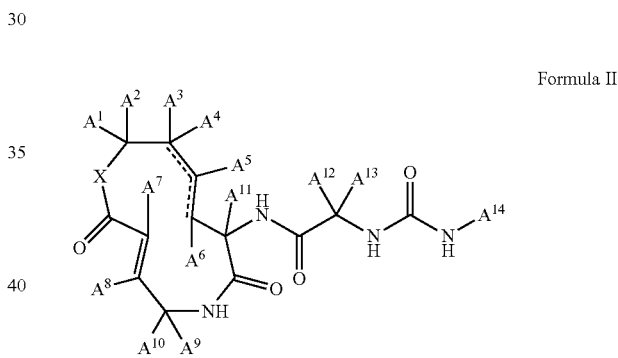

or a pharmaceutically acceptable salt, solvate or prodrug thereof, wherein:

X is N, O or S;

$A^1$-$A^4$ are each independently selected from the group comprising hydrogen, deuterium, FG, optionally substituted ($C_1$-$C_6$)alkyl, optionally substituted ($C_1$-$C_6$)alkenyl, optionally substituted ($C_1$-$C_6$)alkynyl, optionally substituted ($C_1$-$C_5$)hetero-alkyl, optionally substituted ($C_1$-$C_5$)hetero-alkenyl, optionally substituted ($C_1$-$C_5$)hetero-alkynyl, and $A^1$ and $A^4$ can be linked together to form an optionally substituted ring selected from cycloalkyl, heterocycle, and aryl.

$A^5$-$A^9$, $A^{11}$ and $A^{14}$ are each independently selected from the group comprising hydrogen, deuterium, hydroxyl, halo, cyano, amino, nitro, ether, ester, optionally substituted ($C_1$-$C_6$)alkyl, optionally substituted ($C_1$-$C_6$)alkenyl, optionally substituted ($C_1$-$C_6$)alkynyl, optionally substituted ($C_1$-$C_5$) hetero-alkyl, optionally substituted ($C_1$-$C_5$)hetero-alkenyl, and optionally substituted ($C_1$-$C_5$)hetero-alkynyl;

$A^{10}$ is selected from the group comprising hydrogen, deuterium, hydroxyl, halo, cyano, amino, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$) hetero-alkenyl, and optionally substituted ($C_1$-$C_3$)hetero-alkynyl;

$A^{12}$ is selected from the group comprising hydrogen, deuterium, hydroxyl, halo, cyano, amino, amide, carboxylic acid, nitro, ether, ester, optionally substituted ($C_1$-$C_8$)alkyl, optionally substituted ($C_1$-$C_8$)alkenyl, optionally substituted ($C_1$-$C_8$)alkynyl, optionally substituted ($C_1$-$C_7$)hetero-alkyl, optionally substituted ($C_1$-$C_7$)hetero-alkenyl, optionally substituted ($C_1$-$C_7$)hetero-alkynyl, optionally substituted cycloalkyl, optionally substituted aryl, and optionally substituted heterocycle;

$A^{13}$ are each independently selected from the group comprising hydrogen, deuterium, hydroxyl, halo, cyano, amino, amide, carboxylic acid, nitro, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$)hetero-alkenyl, optionally substituted ($C_1$-$C_3$)hetero-alkynyl, optionally substituted cycloalkyl, optionally substituted aryl, and optionally substituted heterocycle, and $A^{12}$ and $A^{13}$ can be linked together to form an optionally substituted ring selected from cycloalkyl, heterocycle, and aryl; and $A^{15}$ is selected from the group comprising hydrogen, deuterium, FG, optionally substituted ($C_1$-$C_{20}$)alkyl, optionally substituted ($C_1$-$C_{20}$)alkenyl, optionally substituted ($C_1$-$C_{20}$)alkynyl, optionally substituted ($C_1$-$C_{20}$)hetero-alkyl, optionally substituted ($C_1$-$C_{20}$)hetero-alkenyl, optionally substituted ($C_1$-$C_{20}$)hetero-alkynyl, optionally substituted cycloalkyl, optionally substituted aryl, and optionally substituted heterocycle.

In another embodiment, the disclosure provides for one or more compounds comprising a structure of Formula II(a):

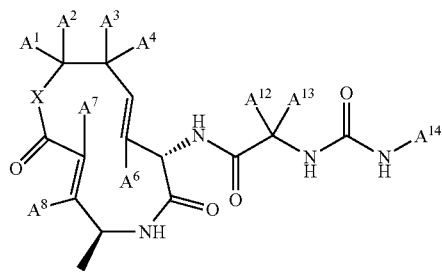

Formula II(a)

or a pharmaceutically acceptable salt, solvate or prodrug thereof, wherein:

X is N, O or S;

$A^1$-$A^4$ are each independently selected from the group comprising hydrogen, deuterium, FG, optionally substituted ($C_1$-$C_6$)alkyl, optionally substituted ($C_1$-$C_6$)alkenyl, optionally substituted ($C_1$-$C_6$)alkynyl, optionally substituted ($C_1$-$C_5$)hetero-alkyl, optionally substituted ($C_1$-$C_5$)hetero-alkenyl, optionally substituted ($C_1$-$C_5$)hetero-alkynyl, and $A^1$ and $A^4$ can be linked together to form an optionally substituted ring selected from cycloalkyl, heterocycle, and aryl.

$A^6$-$A^8$ are each independently selected from the group comprising hydrogen, deuterium, hydroxyl, halo, cyano, amino, nitro, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$)hetero-alkenyl, and optionally substituted ($C_1$-$C_3$)hetero-alkynyl;

$A^{12}$ is selected from the group comprising hydrogen, deuterium, hydroxyl, halo, cyano, amino, amide, carboxylic acid, nitro, ether, ester, optionally substituted ($C_1$-$C_8$)alkyl, optionally substituted ($C_1$-$C_8$)alkenyl, optionally substituted ($C_1$-$C_8$)alkynyl, optionally substituted ($C_1$-$C_7$)hetero-alkyl, optionally substituted ($C_1$-$C_7$)hetero-alkenyl, optionally substituted ($C_1$-$C_7$)hetero-alkynyl, optionally substituted cycloalkyl, optionally substituted aryl, and optionally substituted heterocycle;

$A^{13}$ is selected from the group comprising hydrogen, deuterium, hydroxyl, halo, cyano, amino, amide, carboxylic acid, nitro, ether, ester, optionally substituted ($C_1$-$C_4$)alkyl, optionally substituted ($C_1$-$C_4$)alkenyl, optionally substituted ($C_1$-$C_4$)alkynyl, optionally substituted ($C_1$-$C_3$)hetero-alkyl, optionally substituted ($C_1$-$C_3$)hetero-alkenyl, optionally substituted ($C_1$-$C_3$)hetero-alkynyl, optionally substituted cycloalkyl, optionally substituted aryl, and optionally substituted heterocycle, and $A^{12}$ and $A^{13}$ can be linked together to form an optionally substituted ring selected from cycloalkyl, heterocycle, and aryl; and $A^{14}$ is selected from the group comprising hydrogen, deuterium, FG, optionally substituted ($C_1$-$C_{16}$)alkyl, optionally substituted ($C_1$-$C_{16}$)alkenyl, optionally substituted ($C_1$-$C_{16}$)alkynyl, optionally substituted ($C_1$-$C_{15}$)hetero-alkyl, optionally substituted ($C_1$-$C_{15}$)hetero-alkenyl, optionally substituted ($C_1$-$C_{15}$)hetero-alkynyl, optionally substituted cycloalkyl, optionally substituted aryl, and optionally substituted heterocycle.

In a certain embodiment, the disclosure provides for one or more compounds selected from:

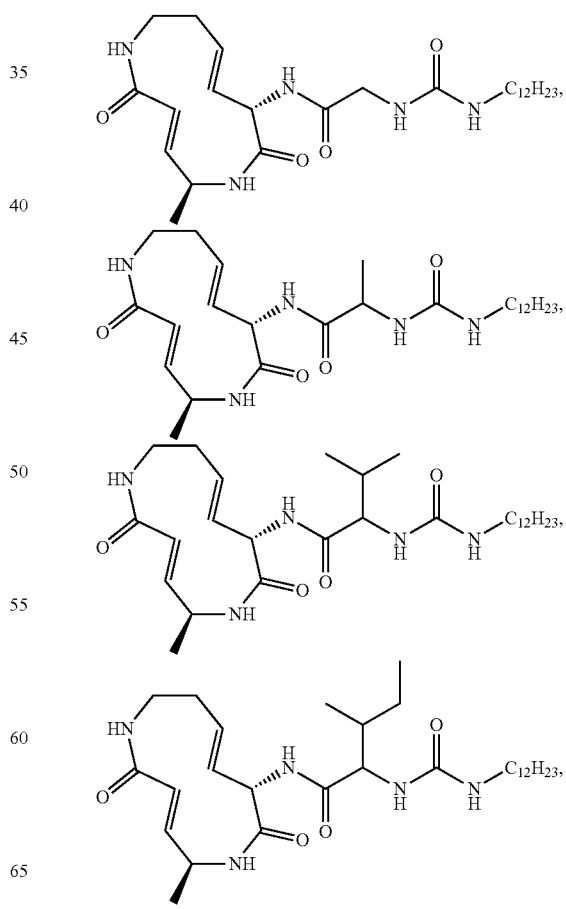

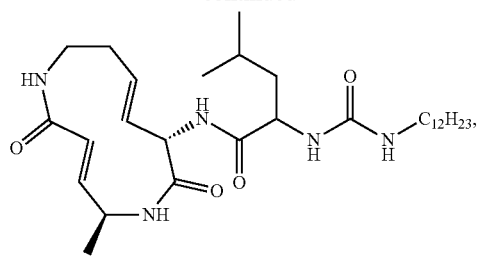
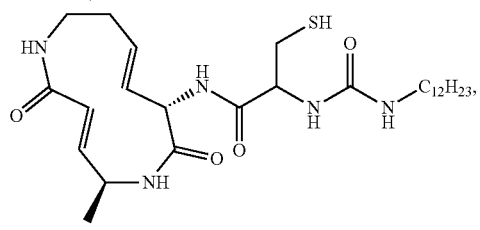
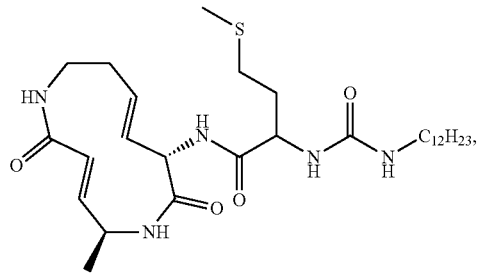
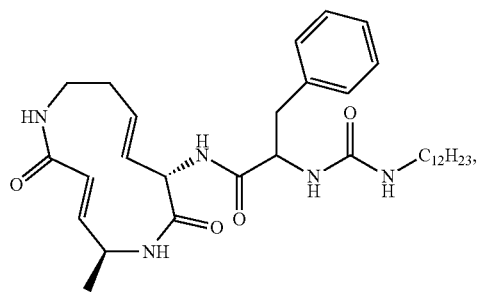
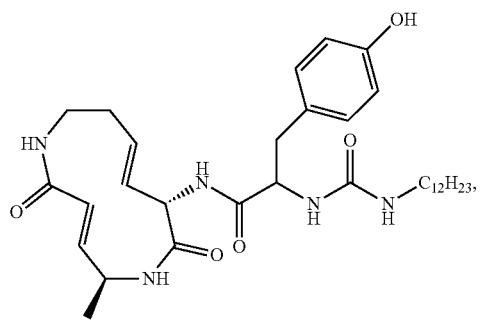
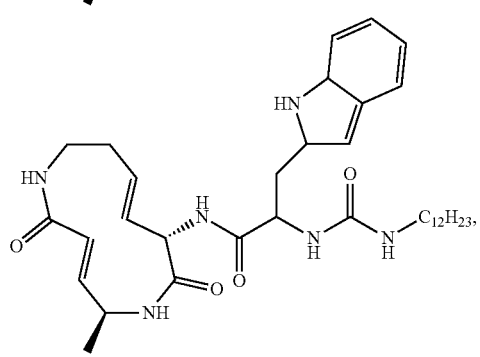
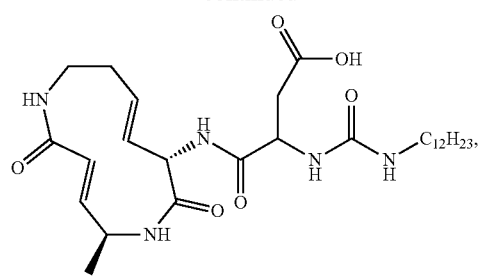
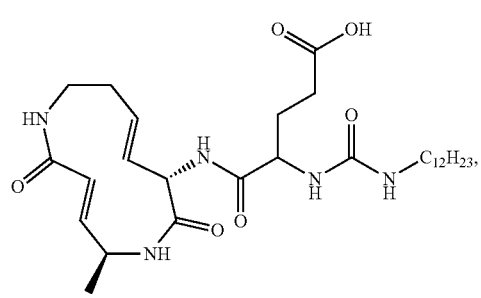
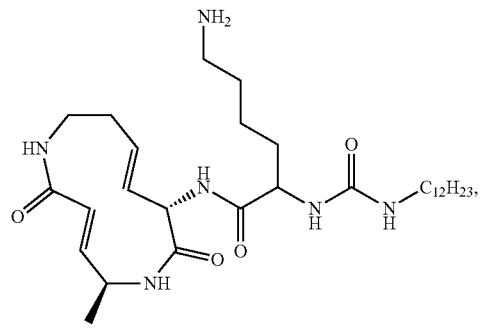
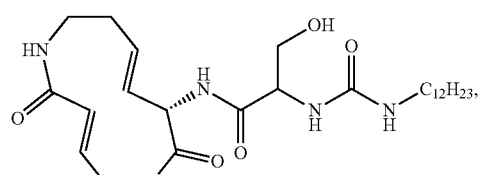
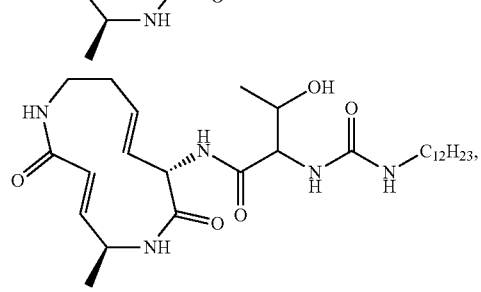
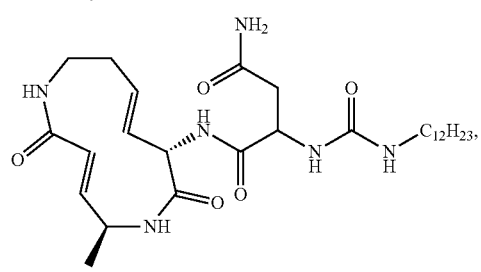

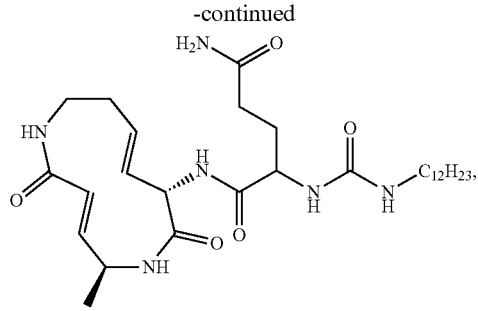
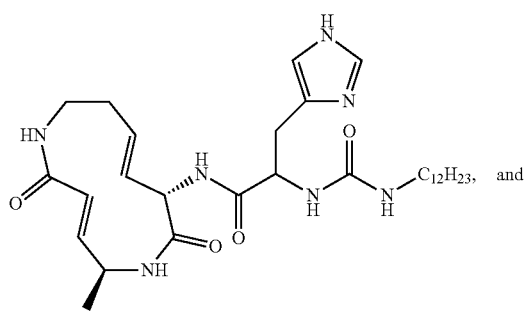
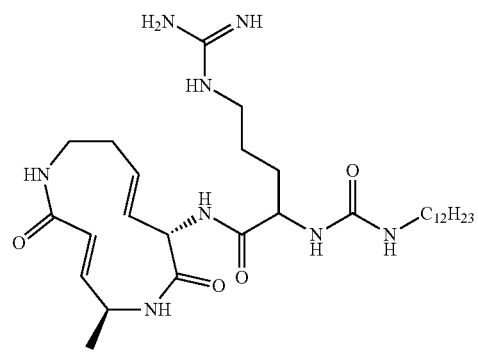
or a pharmaceutically acceptable salt, solvate or prodrug thereof.
In an alternate embodiment, the disclosure provides for one or more compounds selected from:
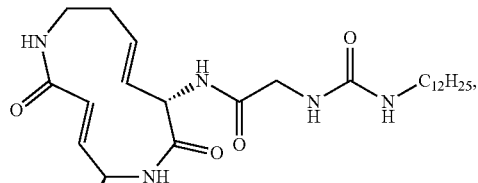
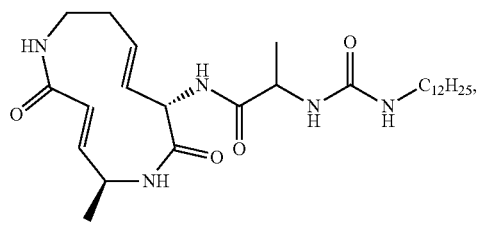
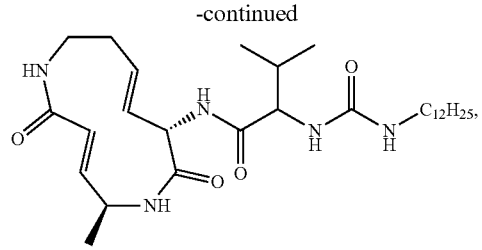
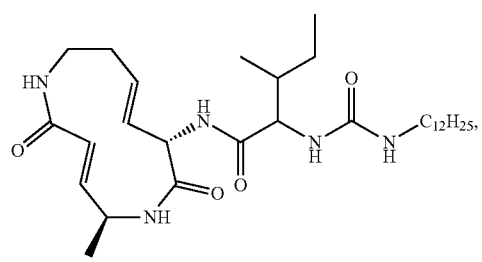
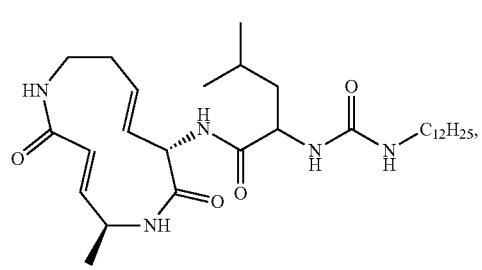
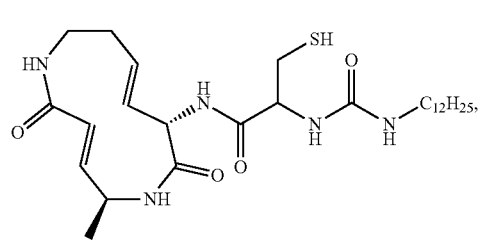
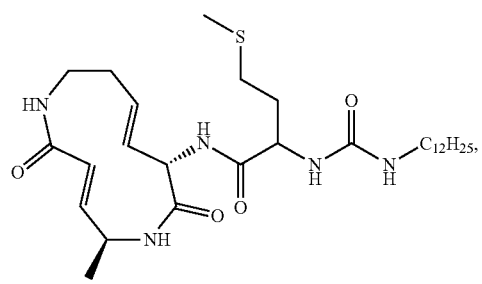
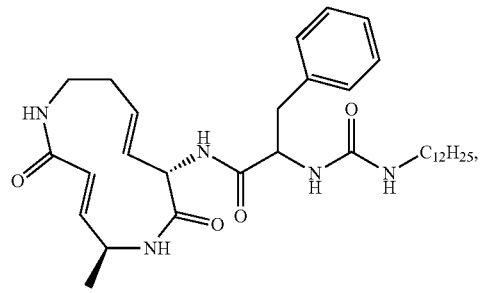

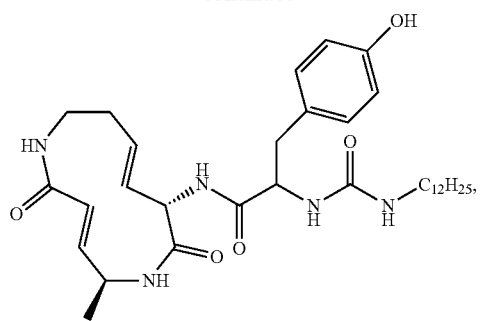
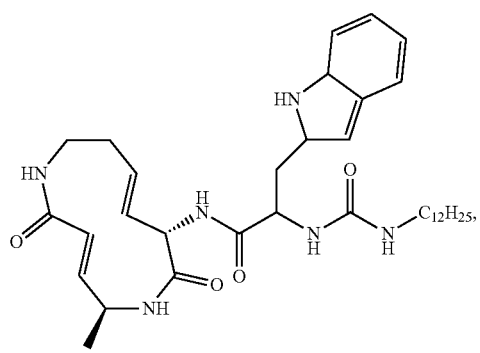
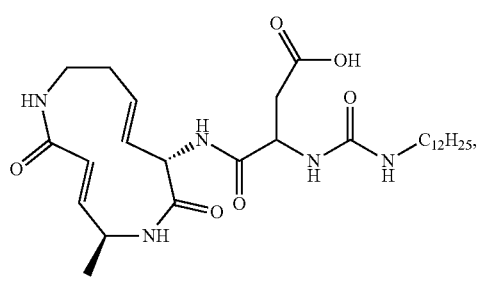
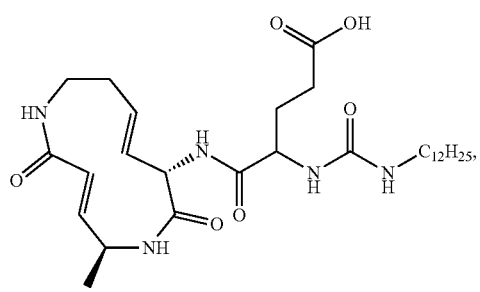
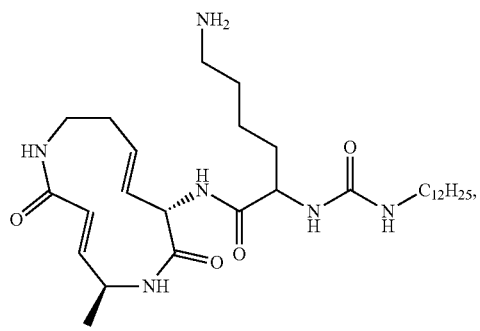
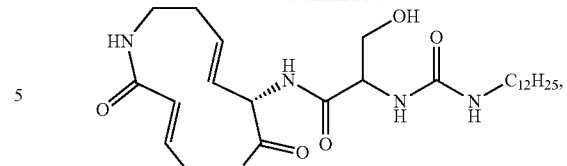
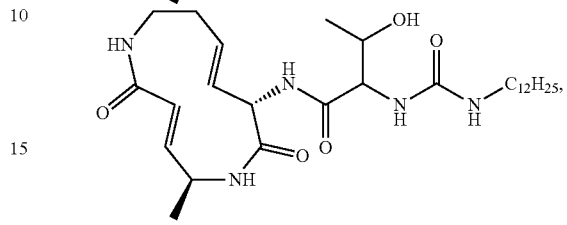
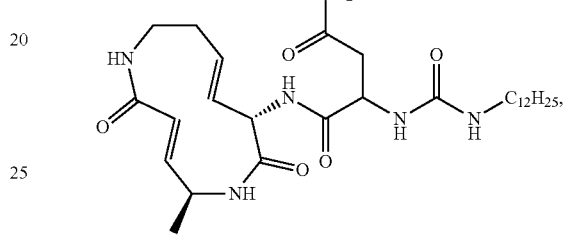
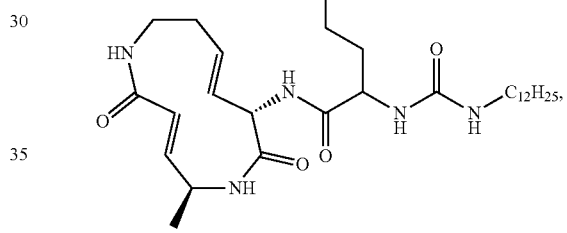
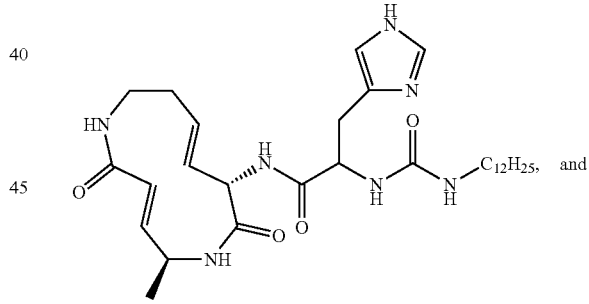
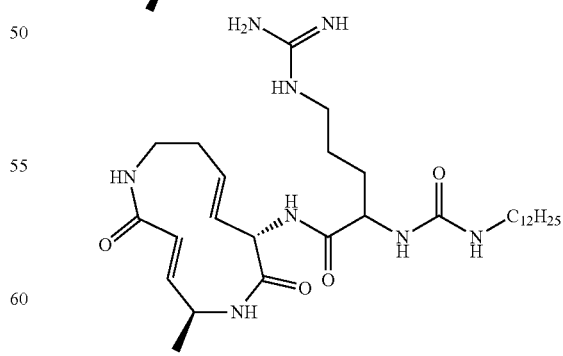
or a pharmaceutically acceptable salt, solvate or prodrug thereof.
In yet another embodiment, the disclosure provides for one or more compounds comprising a structure of Formula II(b):

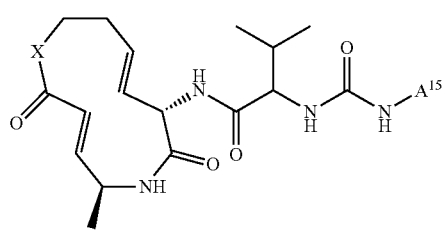

Formula II(b)

or a pharmaceutically acceptable salt, solvate or prodrug thereof, wherein,

X is N, or O;

$A^{15}$ is selected from the group comprising hydrogen, deuterium, FG, optionally substituted $(C_1-C_{16})$alkyl, optionally substituted $(C_1-C_{16})$alkenyl, optionally substituted $(C_1-C_{16})$alkynyl, optionally substituted $(C_1-C_{15})$hetero-alkyl, optionally substituted $(C_1-C_{15})$hetero-alkenyl, optionally substituted $(C_1-C_{15})$hetero-alkynyl, optionally substituted cycloalkyl, optionally substituted aryl, and optionally substituted heterocycle.

In a particular embodiment, the disclosure provides for a compound having the structure selected from the group comprising:

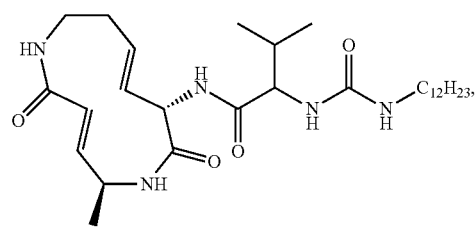

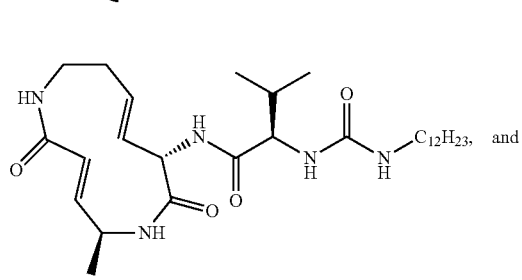

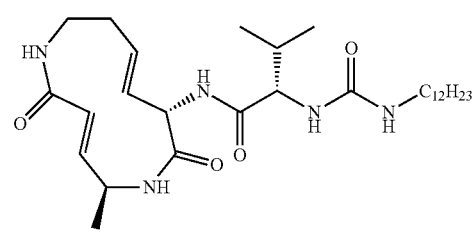

or a pharmaceutically acceptable salt, solvate or prodrug thereof.

In an alternate embodiment, the disclosure provides for a compound having the structure selected from the group comprising:

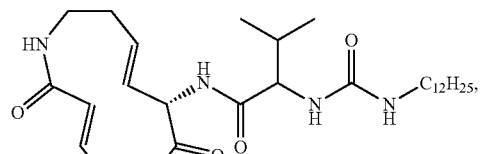

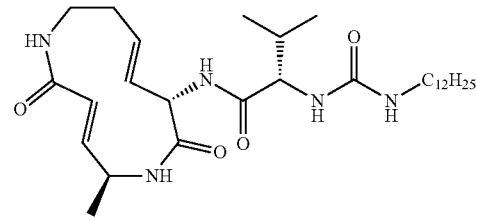

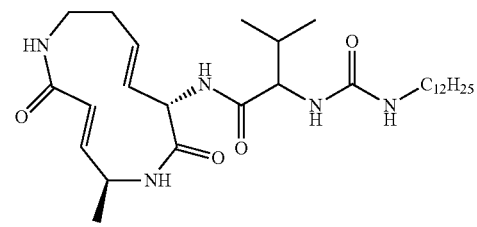

or a pharmaceutically acceptable salt, solvate or prodrug thereof.

In a certain embodiment, a compound of the disclosure has the structure of:

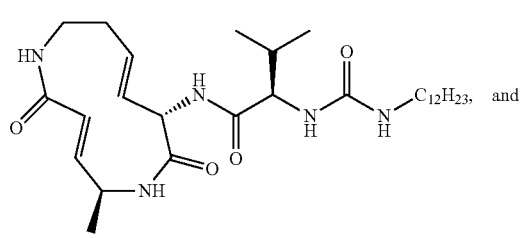

or a pharmaceutically acceptable salt, solvate or prodrug thereof.

In an alternate embodiment, a compound of the disclosure has the structure of:

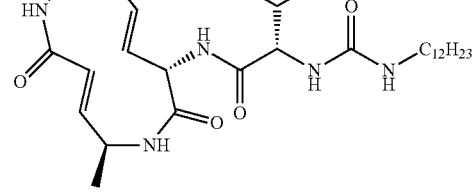

or a pharmaceutically acceptable salt, solvate or prodrug thereof.

The disclosure further provides in a particular embodiment that where a compound disclosed herein contains an alkenyl or alkenylene group, the compound may exist as geometric cis/trans (or Z/E) isomers. Further, where structural isomers are interconvertible via a low energy barrier, the compound disclosed herein may exist as a single tautomer or a mixture of tautomers. This can take the form of proton tautomerism in the compound disclosed herein that contains for example, an imino, keto, or oxime group; or so-called valence tautomerism in the compound that contain an aromatic moiety. It follows that a single compound may exhibit more than one type of isomerism.

The compounds disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

Disclosed herein are pharmaceutical compositions comprising one or more compounds disclosed herein, or a pharmaceutically acceptable salt, solvate, or prodrug thereof, as an active ingredient, combined with a pharmaceutically acceptable vehicle, carrier, diluent, or excipient, or a mixture thereof; in combination with one or more pharmaceutically acceptable excipients or carriers When the compound disclosed herein contains an acidic or basic moiety, it may also disclosed as a pharmaceutically acceptable salt. Examples of pharmaceutically acceptable salts can be found in Berge et al., *J. Pharm. Sci.* 66:1-19 (1977); and "Handbook of Pharmaceutical Salts, Properties, and Use," Stah and Wermuth, Ed., Wiley-VCH and VHCA, Zurich, 2002, which are incorporated herein.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, include, but are not limited to: inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound as disclosed herein may also be designed as a prodrug, which is a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. The following references which are incorporated herein, provide methods to design and make prodrugs of the disclosure: Harper, *Progress in Drug Research* 4:221-294 (1962); Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 5:265-287 (1999); Pauletti et al., *Adv. Drug. Delivery Rev.* 27:235-256 (1997); Mizen et al., *Pharm. Biotech.* 11:345-365 (1998); Gaignault et al., *Pract. Med. Chem.* 671-696 (1996); Asgharnejad in "Transport Processes in Pharmaceutical Systems," Amidon et al., Ed., Marcell Dekker, 185-218, 2000; Balant et al., *Eur. J. Drug Metab. Pharmacokinet.* 15: 143-53 (1990); Balimane and Sinko, *Adv. Drug Delivery Rev.* 39: 183-209 (1999); Browne, *Clin. Neuropharmacol.* 201-12 (1997); Bundgaard, *Arch. Pharm. Chem.* 86:1-39 (1979); Bundgaard, *Controlled Drug Delivery* 17:179-96 (1987); Bundgaard, *Adv. Drug Delivery Rev.* 8:1-38 (1992); Fleisher et al., Adv. Drug Delivery Rev. 19:115-130 (1996); Fleisher et al., *Methods Enzymol.* 112:360-381 (1985); Farquhar et al., *J. Pharm. Sci.* 72:324-325 (1983); Freeman et al., *J. Chem. Soc., Chem. Commun.* 875-877 (1991); Friis and Bundgaard, *Eur. J. Pharm. Sci.* 4:49-59 (1996); Gangwar et al., Des. Biopharm. Prop. Prodrugs Analogs, 409-421 (1977); Nathwani and Wood, *Drugs* 45:866-94 (1993); Sinhababu and Thakker, *Adv. Drug Delivery Rev.* 19:241-273 (1996); Stella et al., *Drugs* 29:455-73 (1985); Tan et al., *Adv. Drug Delivery Rev.* 39:117-151 (1999); Taylor, *Adv. Drug Delivery Rev.* 19:131-148 (1996); Valentino and Borchardt, *Drug Discovery Today* 2:148-155 (1997); Wiebe and Knaus, *Adv. Drug Delivery Rev.* 39:63-80 (1999); Waller et al., *Br. J. Clin. Pharmac.* 28:497-507 (1989).

Disclosed herein are pharmaceutical compositions in modified release dosage forms, which comprise a compound as disclosed herein, or a pharmaceutically acceptable salt, solvate, or prodrug thereof, and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions disclosed herein may also comprise non-release controlling excipients or carriers.

As described herein, the pharmaceutical compositions of the disclosure additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and techniques for the preparation thereof, which is incorporated herein in its entirety. Except insofar as any conventional carrier medium is incompatible with the compounds of the disclosure, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil, safflower oil, sesame oil, olive oil, corn oil and soybean oil; glycols, such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

The disclosure provides in a particular embodiment, pharmaceutical compositions in enteric coated dosage forms, which comprise a compound as disclosed herein, or a pharmaceutically acceptable salt, solvate, or prodrug thereof, and one or more release controlling excipients or carriers for use in an enteric coated dosage form. In a further embodiment, the pharmaceutical compositions may also comprise non-release controlling excipients or carriers.

The disclosure further provides in a certain embodiment, pharmaceutical compositions in effervescent dosage forms, which comprise a compound as disclosed herein, or a pharmaceutically acceptable salt, solvate, or prodrug thereof, and one or more release controlling excipients or carriers for use in an effervescent dosage form. In another embodiment, the pharmaceutical compositions may also comprise non-release controlling excipients or carriers.

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-.beta.-cyclodextrin, sulfobutylether-.beta.-cyclodextrin, and sulfobutylether 7-β-cyclodextrin (CAPTISOL®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are formulated as ready-to-use sterile solutions. In another embodiment, the pharmaceutical compositions are formulated as sterile dry soluble products, including lyophilized powders and hypodermic tablets, to be reconstituted with a vehicle prior to use. In yet another embodiment, the pharmaceutical compositions are formulated as ready-to-use sterile suspensions. In yet another embodiment, the pharmaceutical compositions are formulated as sterile dry insoluble products to be reconstituted with a vehicle prior to use. In still another embodiment, the pharmaceutical compositions are formulated as ready-to-use sterile emulsions.

The pharmaceutical compositions disclosed herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Additionally disclosed herein are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound as disclosed herein, or a pharmaceutically acceptable salt, solvate, or prodrug thereof, and one or more release controlling and non-release controlling excipients or carriers, such as those excipients or carriers suitable for a disruptable semi-permeable membrane and as swellable substances.

The disclosure also provides herein, pharmaceutical compositions in a dosage form for oral administration to a subject, which comprise a compound as disclosed herein, or a pharmaceutically acceptable salt, solvate, or prodrug thereof, and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In a particular embodiment, the disclosure provides for pharmaceutical compositions that comprise about 0.1 to about 1000 mg/mL, about 1 to about 500 mg/mL, about 2 to about 100 mg/mL, about 10 mg/mL to 1 mg/mL, about 5 mg/mL to 1 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 10 mg/mL, about 15 mg/mL, about 20 mg/mL, about 30 mg/mL, about 40 mg/mL, about 50 mg/mL, about 100 mg/mL, about 500 mg/mL of one or more compounds as disclosed herein, for administering intravenously or subcutaneously. The pharmaceutical compositions may further comprise inactive ingredients such as mannitol, sodium chloride, and sorbitol.

In another embodiment, the disclosure provides for pharmaceutical compositions that comprise about 0.1 to about 1000 mg, about 1 to about 500 mg, about 2 to about 100 mg, about 1 mg, about 2 mg, about 3 mg, about 5 mg, about 10 mg, about 15 mg, about 20 mg, about 30 mg, about 40 mg, about 50 mg, about 100 mg, about 500 mg of one or more compounds as disclosed herein, in the form of pills or tablets for oral administration. In yet another embodiment, the pharmaceutical compositions may further comprise inactive ingredients such as ethylcellulose, dibutyl sebacate, polyvinyl pyrroliodone, sodium stearyl fumarate, colloidal silicon dioxide, and polyvinyl alcohol.

The pharmaceutical compositions disclosed herein may be disclosed in "unit-dosage forms" or "multiple-dosage forms." "Unit-dosage forms," as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit-dosage forms may be administered in fractions or multiples thereof. A "multiple-dosage form" as used herein, refers to a plurality of identical unit-dosage forms packaged in a single container to be administered in segregated unit-dosage form. Examples of multiple-dosage forms include vials, bottles of tablets or capsules, or bottles of pints or gallons.

The compound as disclosed herein may be administered alone, or in combination with one or more other compounds disclosed herein, and one or more other active ingredients. The disclosure further provides that a pharmaceutical composition disclosed herein may be formulated for various dosage forms for a particular mode of administration, including oral, parenteral, and topical administration. The pharmaceutical compositions of the disclosure may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see e.g., Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

Administration of the pharmaceutical compositions disclosed herein may begin after the subject is determined to have a disorder or suspected of having a disorder which is treatable by a compound disclosed herein. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters)) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or di-calcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release a compound of the disclosure only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The compounds disclosed herein can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compound of the disclosure may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of the disclosure include ointments, pastes, creams, lotions, gels, powders, solutions, sprays, aerosols, inhalants or patches. A compound disclosed herein is admixed under sterile conditions with a pharmaceutically acceptable carrier and any preservatives or buffers, as may be required. Ophthalmic formulation, ear drops, and eye drops are also contemplated as being within the scope of this disclosure. Additionally, the disclosure contemplates the use of transdermal patches, which have the added advantage of providing controlled delivery of a compound disclosed herein to the body. Such dosage forms are made by dissolving or dispensing a compound of the disclosure in a proper medium. Absorption enhancers can also be used to increase the flux of the compound across the skin. The rate can be controlled by either providing a rate controlling membrane or by dispersing the compound in a polymer matrix or gel.

Depending on the disorder to be treated and the subject's condition, one or more compounds disclosed herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligrams, from about 0.1 to about 500 milligrams, or from 0.5 about to about 100 milligrams active ingredient(s) per dosage unit, and if the condition of the patient requires, the dose can, by way of alternative, be administered as a continuous infusion.

In a certain embodiment, an appropriate dosage level for a compound disclosed herein is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

In a particular embodiment, the compounds disclosed herein can be used as proteasome inhibitors. In a further embodiment, the compounds disclosed herein can be used to selectively inhibit the proteasomes of non-vertebrate organisms. Examples of non-vertebrate organisms, include, organisms from the Eubacteria, Archaebacteria, Fungi, and Protists, and arthropods.

In a certain embodiment, the compounds disclosed herein can be used as a therapeutic agent to treat disorders that are associated with proteasome activity. In a further embodiment, the compounds disclosed herein can be used as a therapeutic to treat disorders that are associated with elevated NF-κB activity (e.g., cancer).

In a particular embodiment, the compounds disclosed herein are anti-cancer and/or anti-neoplastic agents. In a further embodiment, the compounds disclosed herein can be used to treat cancer and/or nonmalignant tumors in a subject. The compounds or pharmaceutical compositions of the disclosure may be administered at a suitable dosage level and a suitable route of administration to effectively treat cancer and/or nonmalignant tumors. Thus, the expression "effective amount" as used herein, refers to a sufficient amount of a compound disclosed herein to induce apoptosis and/or retard the growth of tumor cells.

In another embodiment, the compounds disclosed herein may be used for the treatment of inflammatory disorders, or other disorders affected by proteasome inhibition. Thus, an "effective amount" may also refer to a sufficient amount of a compound disclosed herein so as to treat or ameliorate the symptoms of an inflammatory disorder, or alternatively, a sufficient amount to effectively inhibit proteasome activity. The exact amount of compound required to be effective will vary from subject to subject, depending on the species, age, and general condition of the subject, the severity of the disorder, the type of disorder, mode of administration, and the like.

The compounds of the disclosure are preferably formulated in dosage unit form for ease of administration and uniformity of dosage. It should be understood, however, that the total daily usage of the compounds and pharmaceutical compositions of the disclosure will be decided largely by the attending physician within the scope of sound medical judgment. The specific therapeutically effective dose level for any particular patient or organism will depend upon a variety of factors, including, but not limited to, the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Examples of tumors/cancers which may be treated with the compounds disclosed herein, include, but are not limited to, ovarian, breast (including HER2+ and metastatic), colorectal, colon, renal, rectal, pancreatic, prostate, stomach, gastrointestinal, gastric, esophageal, bile duct, lung (including small cell and non-small cell lung tumors; adenocarcinoma of the lung and squamous carcinoma of the lung), liver, epidermoid tumors, squamous tumors such as head and neck tumors, epithelial squamous cell cancer, thyroid, cervical, neuroendocrine tumors of the digestive system, neuroendocrine tumors, cancer of the peritoneum, hepatocellular cancer, hepatoblastoma, HPCR, glioblastoma, bladder cancer, hepatoma, endometrial or uterine carcinoma, salivary gland carcinoma, kidney or renal cancer, bone cancer, soft tissue sarcoma (including embryonal and alveolar rhabdomyosarcoma, GIST, alveolar soft part sarcoma and clear cell sarcoma), cholangiocarcinoma, bile cancer, gallbladder carcinoma, myeloma, multiple myeloma, vulval cancer, hepatic carcinoma, anal carcinoma, penile carcinoma, retinal, hematopoietic cancer, androgen-dependent tumors, androgen-independent tumors, Kaposi's sarcoma, synovial sarcoma, vasoactive intestinal peptide secreting tumor, CNS neoplasms, neuroblastomas, capillary hemangioblastomas, meningiomas, and cerebral metastases, melanoma, rhabdomyosarcoma, glioblastoma, including glioblastoma multiforme, EMB, RMS, ALV, medulloblastoma, ependymoma, Wilm's cancer, Ewing's cancer, osteosarcoma, PNT, rhabdoid, rhabdomyosarcoma, retinoblastoma, adrenal cortical cancer, adrenal cancer, and leiomyosarcoma. In a certain embodiment, the cancer to be treated is myeloma. In a further embodiment, the cancer to be treated is multiple myeloma. In another embodiment, the cancer to be treated is a kidney cancer.

In a particular embodiment, the compounds disclosed herein can be used as immunomodulators. In a further embodiment, a compound disclosed herein can be used to suppress a subject's immune response. In yet a further embodiment, a compound disclosed herein can be used to treat an autoimmune disorder (e.g., rheumatoid arthritis, lupus erythematosus, and multiple sclerosis) in a subject. In another embodiment, a compound disclosed herein can be used to treat an inflammatory disorder, and/or disorders associated with the activation of the regulatory subunits of the proteasome. These disorders include, but are not limited to inflammation, respiratory distress syndrome, neurological disease (e.g., Alzheimer's Disease), ischemia, cachexia, cystic fibrosis, neoplasm, and HIV infection.

The compounds disclosed herein may also be combined or used in combination with one or more therapeutic agents, including palliative agents, useful in the treatment, prevention, or amelioration of one or more symptoms of a disorder associated with proteasome activity and/or NF-kB activity, such as cancer, nonmalignant tumors, autoimmune disorders, etc. Or, by way of example only, the therapeutic effectiveness of a compound disclosed herein may be enhanced by administration of an adjuvant (i.e., by itself the adjuvant may only have minimal therapeutic benefit, but in combination with another therapeutic agent, the overall therapeutic benefit to the subject is enhanced).

Such other agents, adjuvants, or drugs, may be administered, by a route and in an amount suitable for simultaneous or sequential administration with a compound disclosed herein. When a compound disclosed herein is used contemporaneously with one or more other drugs, a pharmaceutical composition containing such other drugs in addition to the compound disclosed herein may be utilized. Accordingly, the pharmaceutical compositions disclosed herein may also contain one or more other active ingredients or therapeutic agents in addition to a compound disclosed herein, a combination regimen.

The particular combination of therapies (therapeutics or procedures) to employ in a combination regimen will take into account compatibility of the desired therapeutics and/or procedures and the desired therapeutic effect to be achieved. For example, other therapies that may be used in combination with the compounds of the disclosure include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and chemotherapeutic drugs.

In a particular embodiment, one or more compounds disclosed herein can be used in combination with one or more chemotherapeutic agents. Examples of chemotherapeutic agents include, but are not limited to, platinum analogs such as cisplatin and carboplatin; vinblastine; platinum; proteins such as arginine deiminase and asparaginase; alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; antiandrogens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); antimetabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL™, Bristol-Myers Squibb Oncology, Princeton, N.J.) and docetaxel (TAXOTERE™, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofuran; spirogermanium; tenuazonic acid; triaziquone; 2,2',2"-trichlorotriethylamine; urethan; vindesine;

dacarbazine; mannomustine; mitobronitol; mitolactol; pipobroman; gacyto sine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; and capecitabine.

The disclosure provides for the compounds disclosed herein to be administered in combination (e.g., simultaneously or sequentially) with other classes of compounds, including, but not limited to, sepsis treatments, such as drotrecogin-α; antibacterial agents, such as ampicillin; antifungal agents such as terbinafine; anticoagulants, such as bivalirudin; thrombolytics, such as streptokinase; non-steroidal anti-inflammatory agents, such as aspirin; antiplatelet agents, such as clopidogrel; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP inhibitors; calcium channel blockers, such as amlodipine besylate; potassium channel activators; alpha-adrenergic agents; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In another embodiment, the disclosure provides a kit to conveniently and effectively carry out the methods in accordance with the disclosure. In general, the pharmaceutical pack or kit comprises one or more containers filled with one or more of the ingredients of the pharmaceutical compositions of the disclosure. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The following examples are intended to illustrate but not limit the disclosure. While they are typical of those that might be used, other procedures known to those skilled in the art may alternatively be used.

EXAMPLES

Synthesis of the Macrocyclic Ring of Glidobactin

The synthesis of the glidobactin macrocyclic core structure was achieved in five reaction steps and the synthesis of glidobactin was achieved in nine reaction steps. Moreover, the reaction steps are modular (i.e., allows for substitution of reactants) and permit the preparation of many structural variants that could improve on the biological properties of the parent natural products. The ring closing step to form the glidobactin macrocyclic core structure was relatively facile by exploiting a Horner-Wadsworth-Emmons reaction.

The macrocyclic core structure of glidobactin was synthesized using the reactions presented in Scheme III:

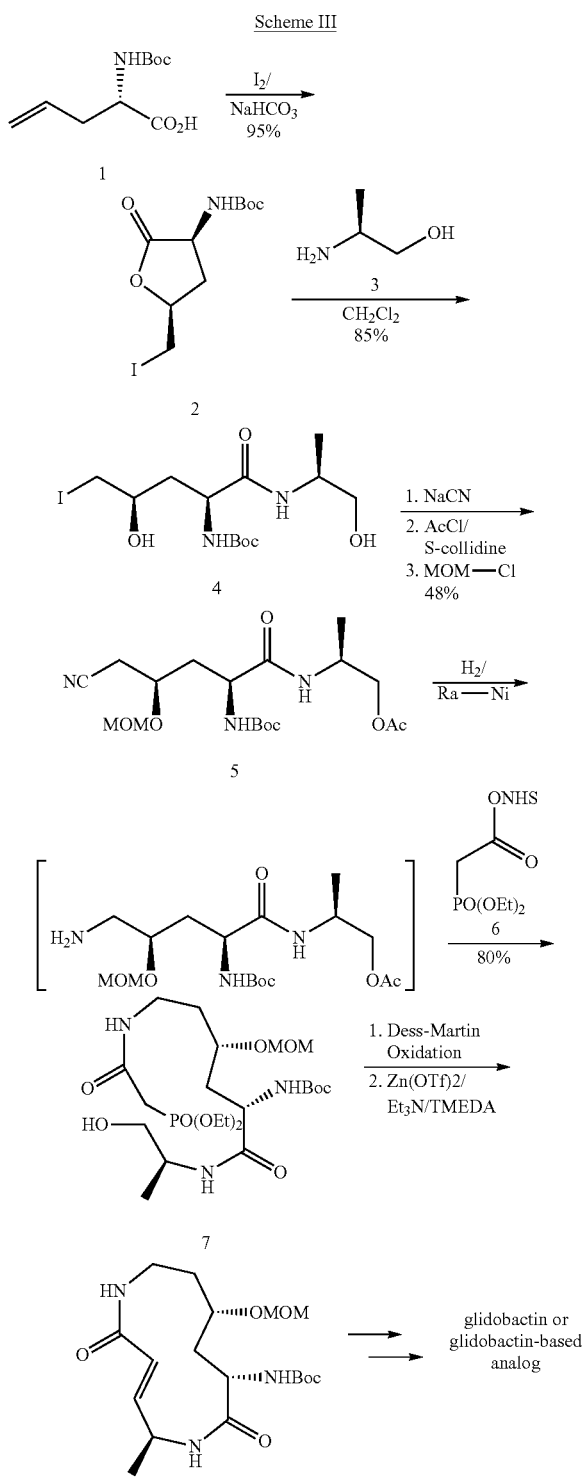

The synthesis began with the preparation of lactone 2. Lactone 2 was then converted to amide 4 by aminolysis. The substitution of iodine with cyanide completed the carbon skeleton of a hydroxylated lysine fragment. The primary alcohol was selectively acylated, and the secondary alcohol was protected with a methoxymethyl ether. The resulting compound 5 was converted by reduction of the nitrile and acylation with a phosphonoacetic acid active ester to give compound 7. This intermediate underwent ring closure using a Horner-Wadsworth-Emmons reaction conditions to afford the macrocyclic core structure 8. The macrocyclic core structure 8 was then used to synthesize glidobactin in a four-step sequence. By using the reaction schemes presented herein, synthesis of glidobactin and glidobactin analogs can be accomplished in much fewer steps than other synthesis methods known in the art. Moreover, the end products were produced with a good overall yield (16%). Consequently, by following the reaction schemes presented herein, large scale manufacture of glidobactin is now feasible.

Development of a Novel Proteasome Inhibiting Compound, TIR-199.

TIR-199 encompasses the following features: (1) for steric reasons having a methyl group next to the site of reaction with the proteasome as opposed to the bulky isopropyl group seen in syringolin A; (2) having a long alkyl side-chain that resembles the side-chain in glidobactin A; (3) having two double bonds within the macrocycle ring as opposed to syringolin B's one double bond. As seen in FIG. 1, TIR-199 is structurally distinct from syringolins A, glidobactin A, Syla-LIP and bortezomib.

In Vitro NCI 60-cell screens with TIR-199.

TIR-199 activity in inhibiting cancer cell growth was tested in a National Cancer Institute ("NCI") 60-cell screen in triplicate (see FIGS. 3-14).

The NCI 60-cell screens were initially tested with 10 µM dose of TIR-199. TIR-199 effectively suppressed cancer cell growth universally across the cell lines at the 10 µM dosage. Due to the initial results being so promising, a full dose-response study was performed in triplicate with the NCI cell lines. In the dose-response study, the most sensitive cell line to TIR-199 was found to be OVCAR-5, with an $IC_{50}$ of 10 nM. Particular potency was also observed against the NCI-H226 lung cancer line, which is one of the NCI 60 cell lines that is most sensitive to the proteasome inhibitor salinosporamide, currently in several clinical trials. Other particularly sensitive cell lines include RXF 393 and TK-10 renal cancer, HCC-2998 colon cancer, PC3 prostate cancer, and BT-549 breast cancer. The effectiveness of TIR-199 on kidney cancer activity was surprisingly potent.

In Vitro Cell-Based Screens with TIR-199.

Further, confirmatory in-vitro experiments have been performed in various laboratories that demonstrate that TIR-199 has low nanomolar potency against cancerous cell lines. Additional studies with multiple myeloma cell lines have shown that TIR-199 is nearly as potent as the FDA approved proteasome inhibitor, bortezomib.

Hollow Fiber Studies.

A panel of at least 12 tumor cell lines is used for the hollow fiber screening of the in vitro actives of the compounds disclosed herein. The panel includes HCC-2998, BT-549, TK-10, RXF 393, OVCAR-5, and at least 7 of the following cell lines: NCI-H23, NCI-H522, MDA-MB-231, MDA-MB-435, SW-620, COLO 205, LOX, UACC-62, OVCAR-3, U251 and SF-295. The cell lines are cultivated in RPMI-1640 containing 10% FBS and 2 mM glutamine. On the day preceding hollow fiber preparation, the cells are given a supplementation of fresh medium to maintain log phase growth. For fiber preparation, the cells are harvested by standard trypsinization technique and re-suspended at the desired cell density ($(2-10 \times 10^6$ cells/ml)). The cell suspension is flushed into 1 mm (internal diameter) polyvinylidene fluoride hollow fibers with a molecular weight exclusion of 500,000 Da. The hollow fibers are heat-sealed at 2 cm intervals and the samples generated from these seals are placed into tissue culture medium and incubated at 37° C. in 5% $CO_2$ for 24 to 48 hours prior to implantation.

A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line preparation are quantitated for viable cell mass by a stable endpoint MTT assay so that the time zero cell mass is known. Mice are treated with experimental agents starting on day 3 or 4 following fiber implantation and continuing daily for 4 days. Each agent is administered by intraperitoneal injection at 2 dose levels. The doses are based on the maximum tolerated dose (MTD) determined during prior acute toxicity testing. The fibers are collected from the mice on the day following the fourth compound treatment and subjected to the stable endpoint MTT assay.

The optical density of each sample is determined spectrophotometrically at 540 nm and the mean of each treatment group is calculated. The percent net growth for each cell line in each treatment group is calculated and compared to the percent net growth in the vehicle treated controls. A 50% or greater reduction in percent net growth in the treated samples compared to the vehicle control samples is considered a positive result. Each positive result is given a score of 2 and all of the scores are totaled for a given compound. The maximum possible score for an agent is 96 (12 cell lines×2 sites×2 dose levels×2 [score]). A compound is considered for xenograft testing if it has a combined ip+sc score of 20 or greater, a sc score of 8 or greater, or produces cell kill of any cell line at either dose level evaluated.

Xenograft Murine Model.

Six-week-old male triple immune-deficient BNX mice (n=100) are obtained from Frederick Cancer Research and Developmental Center (Frederick, Md.). They are maintained in a specific pathogen-free area in an animal resources facility.

Mice are inoculated s.c. into the right flank with $3 \times 10^7$ mm cells in 100 μl of RPMI 1640, together with 100 μl of Matrigel basement membrane matrix (Becton Dickinson, Bedford, Mass.). When tumor is measurable, mice are assigned into four treatment groups receiving a compound disclosed herein or into a control group. Treatment with compound disclosed herein is given i.v. twice weekly via tail vein at 0.05, 0.1, 0.5, and 1.0 mg/kg for 4 weeks. Subsequently, it is administered once weekly. The control group receives the vehicle alone (0.9% sodium chloride) at the same schedule. Caliper measurements of the longest perpendicular tumor diameters are performed every alternate day to estimate the tumor volume, using the following formula: $4\pi/3 \times (width/2)^2 \times (length/2)$, representing the three-dimensional volume of an ellipse. Animals are sacrificed when their tumors reached 2 cm or when the mice became moribund. Survival is evaluated from the first day of treatment until death.

In Vivo Proteasome Inhibition Assay.

At the time of mouse sacrifice, 1 hour after the last drug injection, cell lysates from whole blood, tumor, liver, and spleen are obtained from mice for fluorometric 20S proteasome inhibition assays, based on the rate of the chymotryptic subunit cleavage of a pentapeptide attached to a fluorescent molecule (AMP), as described previously (Lightcap et al., *Clin. Chem.* 46:673-683 (2000)). Briefly, the assay uses a fluorescence spectrophotometer to detect fluorescence generated upon adding the fluorogenic peptide substrate specific for the chymotryptic activity of the proteasome.

In Vivo Cell Cycle Assays.

At time of sacrifice, 1 hour after the last drug injection, tumors are excised for cell cycle profile study. Tumors are minced into a single cell suspension using a 70-μm cell strainer (Becton Dickinson, Franklin Lakes, N.J.). Cells are first separated by Ficoll-Hypaque density sedimentation, washed in PBS, and then fixed in 70% ethanol and treated with 10 μg/ml RNase (Roche Diagnostics Corp., Indianapolis, Ind.). Cells are next stained with propidium iodide (Sigma), and cell cycle profiles are determined by flow cytometry using Coulter EPICS XL-MCL. Data are analyzed using the Phoenix flow system.

Histopathology.

At the time of sacrifice, tumors are excised from mice, fixed in 10% neutral buffered formalin, and embedded in paraffin according to standard histological procedures. For MVD assays, 5-μm paraffin sections are used for immunohistochemistry for mouse CD34 expression. Slides are deparaffinized and pretreated with 1.0 mm EDTA, pH 8.0 (Zymed, South San Francisco, Calif.) in a steam pressure cooker (Decloaking chamber; BioCare Medical, Walnut Creek, Calif.), followed by washing in distilled water. All further steps are performed at room temperature in a hydrated chamber. Slides are treated with peroxidase block (DAKO, Carpinteria, Calif.) for 5 min to quench endogenous peroxidase activity, followed by a 1:5 dilution of goat serum in 50 mm Tris-Cl (pH 7.4), for 20 min to block nonspecific binding sites. Primary rat anti-murine CD34 antibody (PharMingen, San Diego, Calif.) is applied at 1:100 dilutions in 50 mm Tris-Cl (pH 7.4) with 3% goat serum for 1 h. After washing in 50 mm Tris-Cl (pH 7.4), secondary rabbit anti-rat antibody (DAKO) is applied at 1:200 dilution in 50 mm Tris-Cl (pH 7.4) with 3% goat serum for 30 min. Slides are washed again in 50 mm Tris-Cl (pH 7.4), and goat anti-rabbit horseradish peroxidase-conjugated antibody (Envision detection kit; DAKO) is applied for 30 min. After further washing, immunoperoxidase staining is developed using a 3,3'-diaminobenzidine chromogen kit (DAKO) and counterstained with hematoxylin.

MVD is determined by light microscopy, according to the procedures known in the art (Weidner et al., *N. Engl. J. Med.* 324:1-8 (1991)) without knowledge of the treatment history. Areas of most intense neovascularization are identified by scanning tumor sections at low power magnification (×40) and then counted at high power magnification (×400). At least five separate ×400 fields are analyzed by two investigators in a blinded fashion, using double-headed light microscopy.

The TUNEL assay is performed using the ApopTag kit (Intergen Co., Purchase, N.Y.) on histological specimens fixed in formalin. Nucleotides contained in the reaction buffer are enzymatically added to the DNA using terminal deoxynucleotidyl transferase. Terminal deoxynucleotidyl transferase catalyzes the addition of nucleotide triphosphates to the 3'-OH ends of double-stranded or single-stranded DNA from apoptotic cells. The incorporated nucleotides form an oligomer composed of digoxigenin and unlabeled nucleotide. DNA fragments labeled with the digoxigenin nucleotide are then detected by an antidigoxigenin antibody conjugated to peroxidase, allowing the formation of chromogenic substrates visible by light microscopy. H&E staining is also performed on tumor, liver, spleen, bone marrow, heart, lungs, gut, brain, and kidneys and studied for signs of toxicity using light microscopy.

A number of embodiments have been described herein. Nevertheless, it will be understood that various modifications may be made without departing from the spirit and scope of this disclosure. Accordingly, other embodiments are within the scope of the following claims.

What is claimed is:

1. A compound having a structure of Formula II(a):

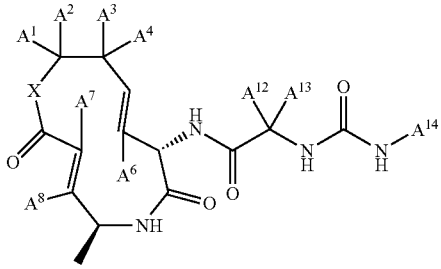

Formula II(a)

or a pharmaceutically acceptable salt thereof, wherein:
X is NH,
$A^1$-$A^4$ are each independently selected from hydrogen, deuterium, $(C_1-C_6)$alkyl, $(C_1-C_6)$alkenyl, $(C_1-C_6)$alkynyl, $(C_1-C_5)$hetero-alkyl, $(C_1-C_5)$hetero-alkenyl, and $(C_1-C_5)$hetero-alkynyl;
$A^6$-$A^8$ are each independently selected from hydrogen, deuterium, hydroxyl, halo, cyano, amino, nitro, alkoxy, alkoxycarbonyl, $(C_1-C_4)$alkyl, $(C_1-C_4)$alkenyl, $(C_1-C_4)$alkynyl, $(C_1-C_3)$hetero-alkyl, $(C_1-C_3)$hetero-alkenyl, and $(C_1-C_3)$hetero-alkynyl;
$A^{12}$ is selected from hydrogen, deuterium, hydroxyl, halo, cyano, amino, carboxamido, carboxyl, nitro, alkoxy, alkoxycarbonyl, $(C_1-C_8)$alkyl, $(C_1-C_8)$alkenyl, $(C_1-C_8)$alkynyl, $(C_1-C_7)$hetero-alkyl, $(C_1-C_7)$hetero-alkenyl, $(C_1-C_7)$hetero-alkynyl, cycloalkyl, aryl, and heterocycle;
$A^{13}$ is selected from hydrogen, deuterium, hydroxyl, halo, cyano, amino, carboxamido, carboxyl, nitro, alkoxy, alkoxycarbonyl, $(C_1-C_4)$alkyl, $(C_1-C_4)$alkenyl, $(C_1-C_4)$alkynyl, $(C_1-C_3)$hetero-alkyl, $(C_1-C_3)$hetero-alkenyl, $(C_1-C_3)$hetero-alkynyl, cycloalkyl, aryl, and heterocycle; and
$A^{14}$ is selected from hydrogen, deuterium, $(C_{12}-C_{16})$alkyl, $(C_{12}-C_{16})$alkenyl, $(C_{12}-C_{16})$alkynyl, $(C_{12}-C_{15})$hetero-alkyl, $(C_{12}-C_{15})$hetero-alkenyl, $(C_{12}-C_{15})$hetero-alkynyl, cycloalkyl, aryl, and heterocycle,
wherein the heteroatoms making up the hetero-alkyl, hetero-alkenyl, hetero-alkynyl, and heterocycle are selected from N, O and/or S.

2. The compound of claim 1, wherein the compound is selected from:

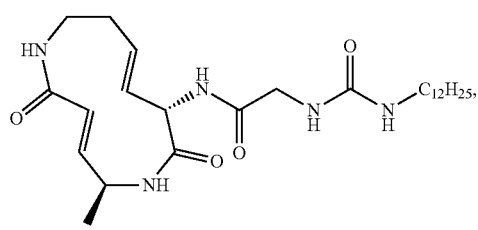

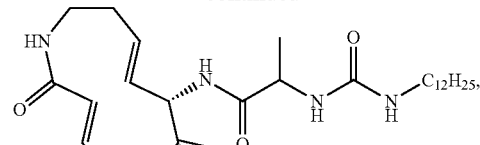

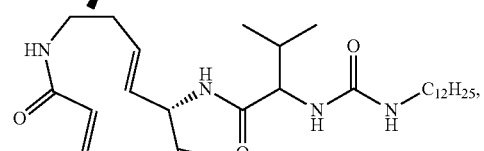

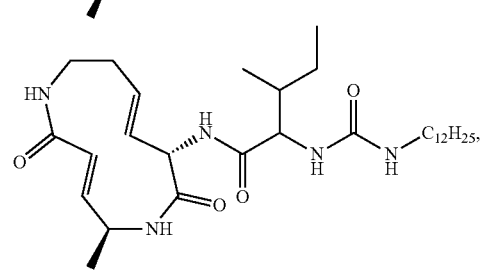

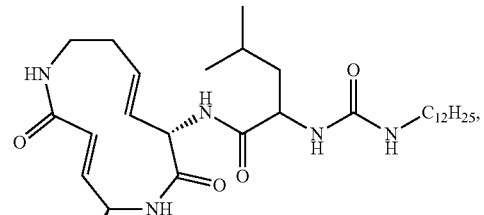

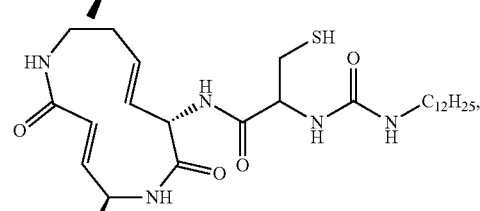

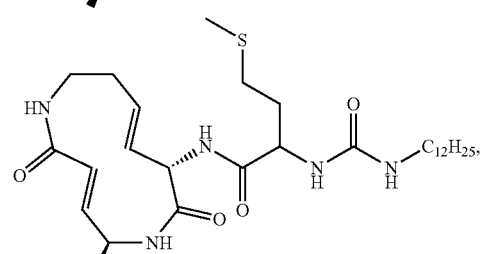

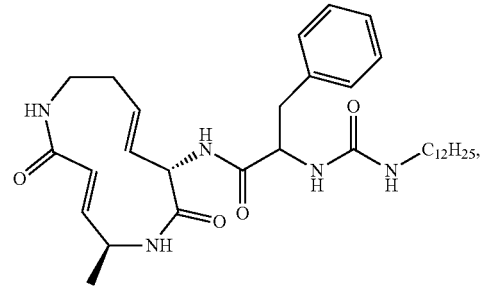

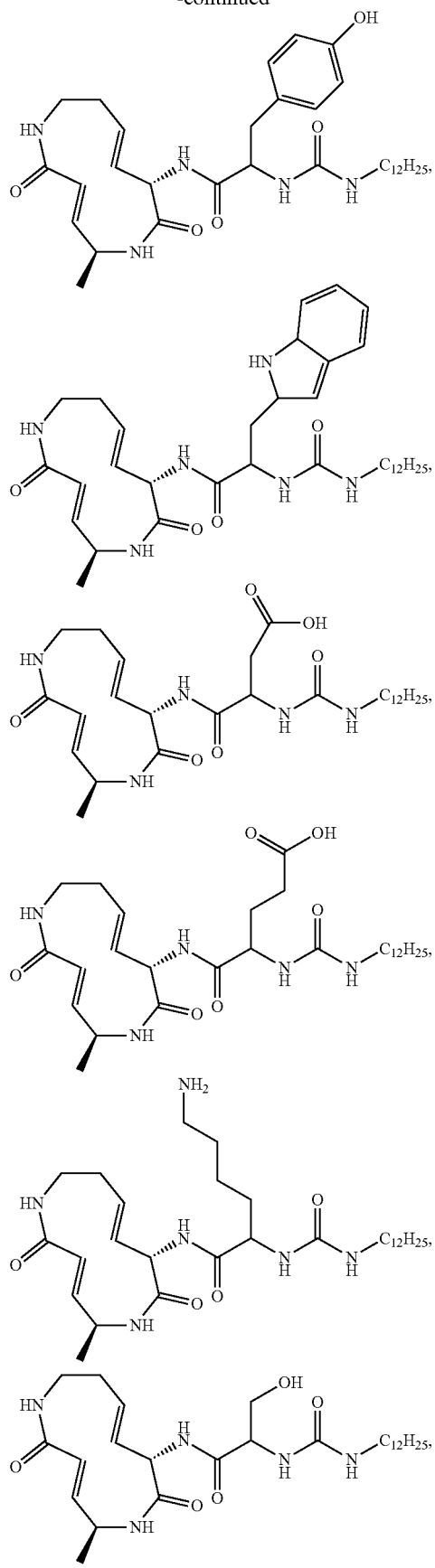
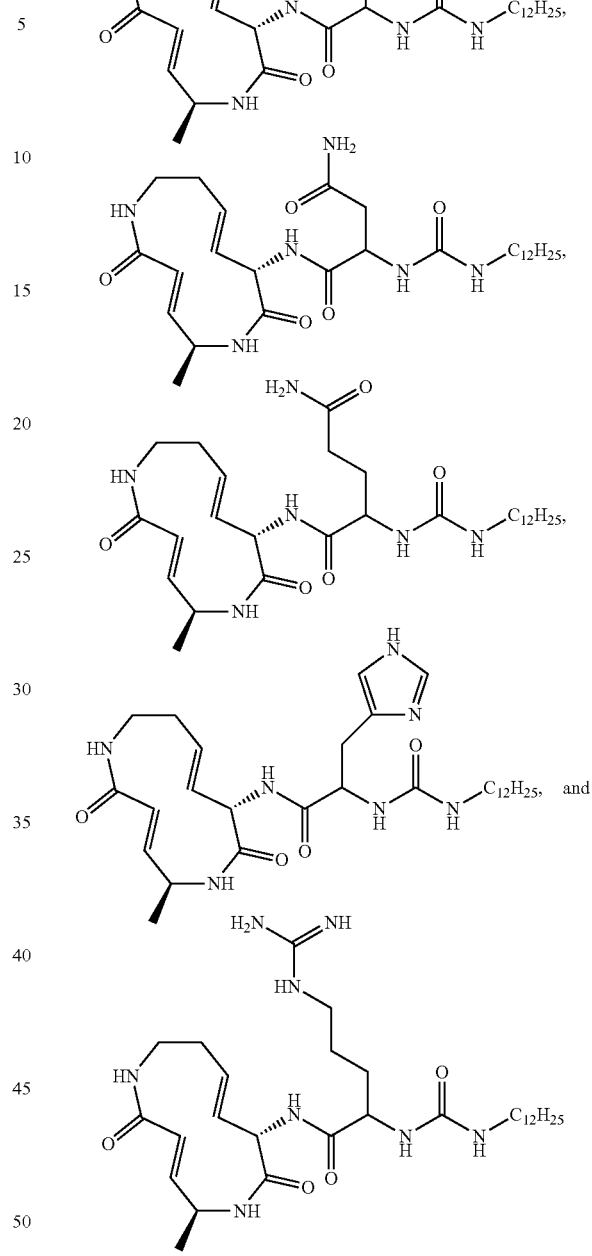
or a pharmaceutically acceptable salt thereof.
3. The compound of claim 1, comprising a structure of Formula II(b):
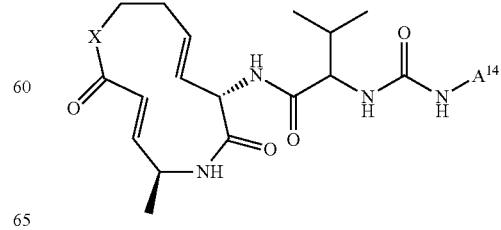
Formula II(b)
or a pharmaceutically acceptable salt thereof, wherein:

X is NH;

A$^{14}$ is selected from hydrogen, deuterium, (C$_{12}$-C$_{16}$)alkyl, (C$_{12}$-C$_{16}$)alkenyl, (C$_{12}$-C$_{16}$)alkynyl, (C$_{12}$-C$_{15}$)hetero-alkyl, (C$_{12}$-C$_{15}$)hetero-alkenyl, (C$_{12}$-C$_{15}$)hetero-alkynyl, cycloalkyl, aryl, and heterocycle, wherein the heteroatoms making up the hetero-alkyl, hetero-alkenyl, hetero-alkynyl, and heterocycle are selected from N, O and/or S.

4. The compound of claim 3, wherein the compound is selected from:

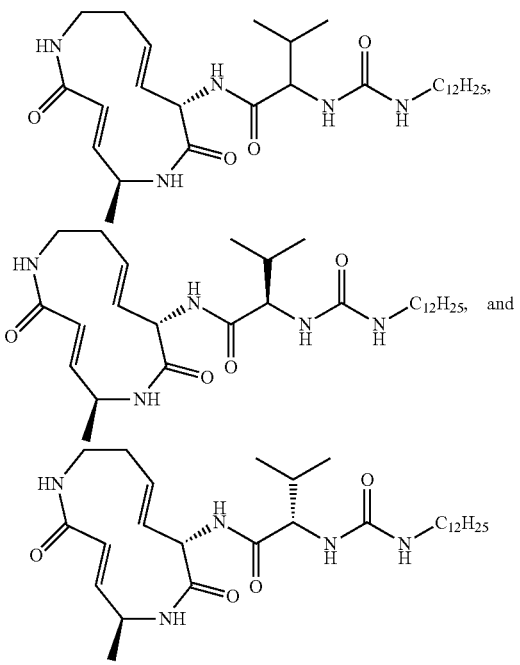

or a pharmaceutically acceptable salt thereof.

5. A compound having the structure of:

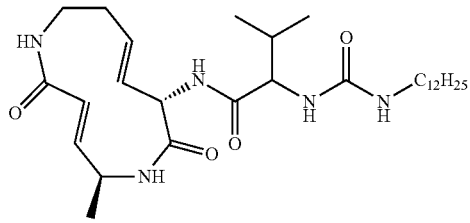

or a pharmaceutically acceptable salt thereof.

6. A pharmaceutical composition comprising the compound of claim 1 and one or more pharmaceutically acceptable carriers.

7. The pharmaceutical composition of claim 6, wherein the composition is formulated to be administered intravenously or subcutaneously.

8. The pharmaceutical composition of claim 7, wherein the intravenous or subcutaneously dose comprises between 1 mg/mL to 5 mg/mL of the compound.

9. A method of treating a subject having or suspected of having a cancer comprising administering a therapeutically effective amount of the compound of claim 1 to the subject in need thereof, wherein the subject has a cancer selected from the group consisting of ovarian cancer, breast cancer, colorectal cancer, colon cancer, rectal cancer, prostate cancer, kidney or renal cancer, CNS neoplasms, neuroblastomas, glioblastomas, melanomas, non-small cell lung cancer and leukemia.

10. The method of claim 9, wherein the cancer is kidney cancer.

11. The method of claim 9, further comprising the administration of one or more additional therapeutic agents.

12. The method of claim 11, wherein the one or more additional therapeutic agents are one or more chemotherapeutic agents.

13. The method of claim 12, wherein the one or more chemotherapeutic agents is selected from cisplatin, carboplatin, vinblastine, platinum, arginine deiminase, asparaginase, thiotepa, cyclosphosphamide, busulfan, improsulfan, piposulfan, calusterone, dromostanolone propionate, epitiostanol, mepitiostane, testolactone, aminoglutethimide, mitotane, trilostane, flutamide, nilutamide, bicalutamide, leuprolide, goserelin, aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, tamoxifen, raloxifene, 4-hydroxytamoxifen, trioxifene, keoxifene, LY 117018, onapristone, toremifene, methotrexate, 5-fluorouracil, denopterin, methotrexate, pteropterin, trimetrexate, benzodopa, carboquone, meturedopa, uredopa, ethylenimines, altretamine, triethylenemelamine, trietylenephosphoramide, triethylenethiophosphaoramide, trimethylolomelamine, frolinic acid, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, paclitaxel, docetaxel, RFS 2000, thymidylate synthase inhibitors, aceglatone, aldophosphamide glycoside, aminolevulinic acid, amsacrine, bestrabucil, bisantrene, edatraxate, defofamine, demecolcine, diaziquone, difluoromethylornithine (DMFO), elformithine, elliptinium acetate, etoglucid, gallium nitrate, hydroxyurea, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, tenuazonic acid, triaziquone, 2,2',2''-trichlorotriethylamine, urethane, vindesine, dacarbazine, mannomustine, mitobronitol, mitolactol, pipobroman, gacyto sine, arabinoside ("Ara-C"), chlorambucil, gemcitabine, 6-thioguanine, mercaptopurine, methotrexate, etoposide, ifosfamide, mitomycin C, mitoxantrone, vincristine, vinorelbine, navelbine, novantrone, teniposide, daunomycin, aminopterin, xeloda, ibandronate, CPT-11, retinoic acid, esperamicins, and capecitabine.

14. The method of claim 12, wherein the one or more chemotherapeutic agents is selected from vinblastine, floxuridine, 5-fluorouracil, capecitabine, gemcitabine, bortezomib, cyclophosphamide, melphalan, doxorubicin, idarubicin, cisplatin, etoposide, and bendamustine.

15. The compound of claim 1, wherein the compound has a structure of Formula II(a):

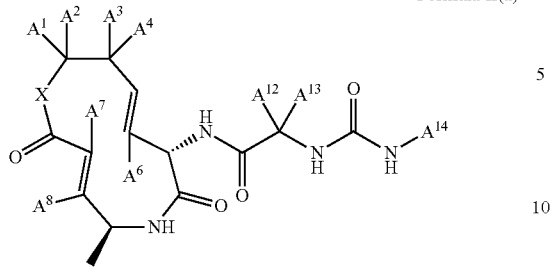
Formula II(a)
or a pharmaceutically acceptable salt thereof, wherein:
X is NH;
$A^1$-$A^4$, $A^6$-$A^8$, $A^{12}$ are hydrogen;
$A^{13}$ is a 1-hydroxyethyl group; and
$A^{14}$ is a ($C_{12}$-$C_{16}$)alkenyl group.
* * * * *